United States Patent
Penner et al.

(10) Patent No.: US 10,085,731 B2
(45) Date of Patent: Oct. 2, 2018

(54) VASCULATURE CLOSURE DEVICES AND METHODS

(71) Applicant: E-Pacing, Inc., Wilmington, DE (US)

(72) Inventors: Abraham Penner, Tel Aviv (IL); Lone Wolinsky, Ramat Gan (IL); Alon Ben-Yosef, Ramot Manasha (IL)

(73) Assignee: E-Pacing, Inc., Wilmington, New Castle County, DE (US)

( * ) Notice: Subject to any disclaimer, the term of this patent is extended or adjusted under 35 U.S.C. 154(b) by 309 days.

(21) Appl. No.: 14/905,456

(22) PCT Filed: Jul. 14, 2014

(86) PCT No.: PCT/US2014/046556
§ 371 (c)(1),
(2) Date: Jan. 15, 2016

(87) PCT Pub. No.: WO2015/009634
PCT Pub. Date: Jan. 22, 2015

(65) Prior Publication Data
US 2016/0151613 A1    Jun. 2, 2016

Related U.S. Application Data

(60) Provisional application No. 61/978,374, filed on Apr. 11, 2014, provisional application No. 61/846,419, filed on Jul. 15, 2013.

(51) Int. Cl.
*A61B 17/08*    (2006.01)
*A61M 29/00*    (2006.01)
(Continued)

(52) U.S. Cl.
CPC ......... *A61B 17/0057* (2013.01); *A61M 29/00* (2013.01); *A61M 29/02* (2013.01);
(Continued)

(58) Field of Classification Search
CPC .. A61M 29/02; A61M 29/00; A61M 2205/04; A61B 17/0057;
(Continued)

(56) References Cited

U.S. PATENT DOCUMENTS

| 4,744,364 A | 5/1988 | Kensey |
| 4,852,568 A | 8/1989 | Kensey |

(Continued)

FOREIGN PATENT DOCUMENTS

| EP | 0362113 A1 | 4/1990 |
| EP | 534696 | 3/1993 |

(Continued)

OTHER PUBLICATIONS

PCT International Search Report and Written Opinion dated Jan. 12, 2015 for PCT/US2014/046556.

(Continued)

*Primary Examiner* — Julian W Woo
(74) *Attorney, Agent, or Firm* — Eversheds Sutherland (US) LLP

(57) ABSTRACT

Vasculature closure devices, and systems and methods for their use, are provided. In one or more embodiments, a vasculature closure device (200) includes an expandable support frame (210) deployable within a vessel (10), and a sealing membrane (205) at least partially supported by the support frame (210). Upon expanding the support frame (210) within the vessel (10), the device is configured to intraluminally position the sealing membrane (205) against a puncture site existing in a wall of the vessel. The sealing membrane includes an area of excess membrane (245) configured to facilitate coupling of the sealing membrane to the wall of the vessel.

30 Claims, 18 Drawing Sheets

(51) Int. Cl.
*A61B 17/00* (2006.01)
*A61M 29/02* (2006.01)

(52) U.S. Cl.
CPC .............. *A61B 2017/00004* (2013.01); *A61B 2017/0061* (2013.01); *A61B 2017/00592* (2013.01); *A61B 2017/00597* (2013.01); *A61B 2017/00615* (2013.01); *A61B 2017/00623* (2013.01); *A61B 2017/00659* (2013.01); *A61M 2205/04* (2013.01)

(58) Field of Classification Search
CPC ........... A61B 2017/00659; A61B 2017/00623; A61B 2017/00615; A61B 2017/0061; A61B 2017/00597; A61B 2017/00592; A61B 2017/00004
See application file for complete search history.

(56) References Cited

U.S. PATENT DOCUMENTS

| | | | |
|---|---|---|---|
| 4,890,612 A | 1/1990 | Kensey | |
| 4,917,089 A | 4/1990 | Sideris | |
| 5,021,059 A | 6/1991 | Kensey et al. | |
| 5,108,421 A | 4/1992 | Fowler | |
| 5,192,300 A | 3/1993 | Fowler | |
| 5,192,302 A | 3/1993 | Kensey et al. | |
| 5,275,616 A | 1/1994 | Fowler | |
| 5,282,827 A | 2/1994 | Kensey | |
| 5,304,184 A | 4/1994 | Hathaway et al. | |
| 5,320,639 A | 5/1994 | Rudnick | |
| 5,340,399 A | 8/1994 | Uftring et al. | |
| 5,370,660 A | 12/1994 | Weinstein et al. | |
| 5,383,896 A | 1/1995 | Gershuny et al. | |
| 5,383,897 A | 1/1995 | Wholey | |
| 5,389,106 A | 2/1995 | Tower | |
| 5,413,571 A | 5/1995 | Katsaros et al. | |
| 5,425,744 A * | 6/1995 | Fagan ................ | A61B 17/0057 606/151 |
| 5,476,469 A | 12/1995 | Hathaway et al. | |
| 5,486,195 A | 1/1996 | Myers et al. | |
| 5,496,332 A | 3/1996 | Sierra et al. | |
| 5,540,715 A | 7/1996 | Katsaros et al. | |
| 5,593,422 A | 1/1997 | Muijs Van De Moer et al. | |
| 5,601,602 A | 2/1997 | Fowler | |
| 5,620,461 A | 4/1997 | Muijs Van De Moer et al. | |
| 5,630,833 A | 5/1997 | Katsaros et al. | |
| 5,645,566 A | 7/1997 | Brenneman et al. | |
| 5,676,689 A | 10/1997 | Kensey et al. | |
| 5,716,375 A | 2/1998 | Fowler | |
| 5,725,551 A | 3/1998 | Myers et al. | |
| 5,779,719 A | 7/1998 | Klein et al. | |
| 5,782,860 A * | 7/1998 | Epstein ............ | A61B 17/00491 606/213 |
| 5,824,054 A | 10/1998 | Khosravi et al. | |
| 5,922,009 A | 7/1999 | Epstein et al. | |
| 5,951,589 A | 9/1999 | Epstein et al. | |
| 6,056,768 A | 5/2000 | Cates et al. | |
| 6,071,300 A | 6/2000 | Brenneman et al. | |
| 6,080,183 A | 6/2000 | Tsugita et al. | |
| 6,126,675 A | 10/2000 | Shchervinsky et al. | |
| 6,162,240 A | 12/2000 | Cates et al. | |
| 6,183,496 B1 | 2/2001 | Urbanski | |
| 6,245,103 B1 | 6/2001 | Stinson | |
| 6,254,628 B1 | 7/2001 | Wallace et al. | |
| 6,261,309 B1 | 7/2001 | Urbanski | |
| 6,296,685 B1 | 10/2001 | Cammann et al. | |
| 6,315,787 B1 | 11/2001 | Tsugita et al. | |
| 6,344,049 B1 | 2/2002 | Levinson et al. | |
| 6,371,974 B1 | 4/2002 | Brenneman et al. | |
| 6,379,382 B1 | 4/2002 | Yang | |
| 6,391,048 B1 | 5/2002 | Ginn et al. | |
| 6,395,015 B1 | 5/2002 | Borst et al. | |
| 6,398,758 B1 | 6/2002 | Jacobsen et al. | |
| 6,409,739 B1 | 6/2002 | Nobles et al. | |
| 6,458,140 B2 | 10/2002 | Akin et al. | |
| 6,547,806 B1 | 4/2003 | Ding | |
| 6,613,070 B2 | 9/2003 | Redmond et al. | |
| 6,626,914 B2 | 9/2003 | Solem | |
| 6,638,293 B1 | 10/2003 | Makower et al. | |
| 6,663,607 B2 | 12/2003 | Slaikeu et al. | |
| 6,699,261 B1 | 3/2004 | Cates et al. | |
| 6,699,262 B2 | 3/2004 | Redmond et al. | |
| 6,709,455 B1 | 3/2004 | Chouinard | |
| 6,719,777 B2 | 4/2004 | Ginn et al. | |
| 6,749,621 B2 | 6/2004 | Pantages et al. | |
| 6,780,197 B2 | 8/2004 | Roe et al. | |
| 6,818,008 B1 | 11/2004 | Cates et al. | |
| 6,911,037 B2 * | 6/2005 | Gainor ............... | A61B 17/0057 606/213 |
| 6,942,674 B2 | 9/2005 | Belef et al. | |
| 6,949,114 B2 | 9/2005 | Milo et al. | |
| 6,962,588 B2 | 11/2005 | Sauvageau et al. | |
| 6,969,397 B2 | 11/2005 | Ginn | |
| 7,022,132 B2 | 4/2006 | Kocur | |
| 7,060,078 B2 | 6/2006 | Hathaway et al. | |
| 7,122,043 B2 | 10/2006 | Greenhalgh et al. | |
| 7,175,646 B2 | 2/2007 | Brenneman et al. | |
| 7,223,266 B2 | 5/2007 | Lindenbaum et al. | |
| 7,316,704 B2 | 1/2008 | Bagaoisan et al. | |
| 7,318,836 B2 | 1/2008 | Brown et al. | |
| 7,331,979 B2 | 2/2008 | Khosravi et al. | |
| 7,331,981 B2 | 2/2008 | Cates et al. | |
| 7,335,220 B2 | 2/2008 | Khosravi et al. | |
| 7,361,183 B2 | 4/2008 | Ginn | |
| 7,488,314 B2 | 2/2009 | Segal et al. | |
| 7,537,609 B2 | 5/2009 | Davidson et al. | |
| 7,544,203 B2 | 6/2009 | Chin et al. | |
| 7,572,274 B2 | 8/2009 | Yassinzadeh | |
| 7,621,936 B2 | 11/2009 | Cragg et al. | |
| 7,658,748 B2 | 2/2010 | Marino et al. | |
| 7,662,161 B2 | 2/2010 | Briganti et al. | |
| 7,892,246 B2 | 2/2011 | Akin et al. | |
| 8,114,125 B2 * | 2/2012 | Seibold ............. | A61B 17/0057 606/215 |
| 8,118,833 B2 | 2/2012 | Seibold et al. | |
| 8,277,481 B2 * | 10/2012 | Kawaura ........... | A61B 17/0057 606/213 |
| 8,317,823 B2 | 11/2012 | Pavcnik et al. | |
| 8,323,305 B2 * | 12/2012 | Epstein ............ | A61B 17/00491 606/191 |
| 8,460,335 B2 | 6/2013 | Carpenter | |
| 8,597,324 B2 * | 12/2013 | Briganti ............ | A61B 17/0057 606/213 |
| 9,554,806 B2 * | 1/2017 | Larsen ............... | A61B 17/0057 |
| 2001/0047202 A1 | 11/2001 | Slaikeu et al. | |
| 2002/0019648 A1 | 2/2002 | Akerfeldt et al. | |
| 2002/0026215 A1 | 2/2002 | Redmond et al. | |
| 2002/0082613 A1 | 6/2002 | Hathaway et al. | |
| 2002/0156495 A1 | 10/2002 | Brenneman et al. | |
| 2002/0165602 A1 | 11/2002 | Douglas et al. | |
| 2002/0193808 A1 | 12/2002 | Belef et al. | |
| 2003/0023267 A1 | 1/2003 | Ginn | |
| 2003/0050664 A1 | 3/2003 | Solem | |
| 2003/0078616 A1 | 4/2003 | Ginn et al. | |
| 2003/0109820 A1 | 6/2003 | Gross et al. | |
| 2003/0125766 A1 | 7/2003 | Ding | |
| 2003/0158578 A1 | 8/2003 | Pantages et al. | |
| 2004/0073255 A1 | 4/2004 | Ginn et al. | |
| 2004/0153122 A1 | 8/2004 | Palermo | |
| 2004/0153123 A1 | 8/2004 | Palermo et al. | |
| 2004/0162578 A1 | 8/2004 | Redmond et al. | |
| 2004/0167570 A1 | 8/2004 | Pantages et al. | |
| 2004/0176798 A1 | 9/2004 | Epstein et al. | |
| 2004/0210244 A1 | 10/2004 | Vargas et al. | |
| 2004/0220610 A1 | 11/2004 | Kreidler et al. | |
| 2004/0260333 A1 | 12/2004 | Dubrul et al. | |
| 2004/0267307 A1 | 12/2004 | Bagaoisan et al. | |
| 2004/0267308 A1 | 12/2004 | Bagaoisan et al. | |
| 2005/0085854 A1 | 4/2005 | Ginn | |
| 2005/0154443 A1 | 7/2005 | Linder et al. | |
| 2005/0228443 A1 | 10/2005 | Yassinzadeh | |
| 2005/0267522 A1 | 12/2005 | Yassinzadeh | |
| 2005/0267528 A1 | 12/2005 | Ginn et al. | |

(56) References Cited

U.S. PATENT DOCUMENTS

| | | |
|---|---|---|
| 2005/0267568 A1 | 12/2005 | Berez et al. |
| 2005/0267570 A1 | 12/2005 | Shadduck |
| 2005/0273136 A1 | 12/2005 | Belef et al. |
| 2005/0277980 A1 | 12/2005 | Yassinzadeh |
| 2006/0106418 A1 | 5/2006 | Seibold et al. |
| 2006/0135991 A1 | 6/2006 | Kawaura et al. |
| 2006/0190036 A1 | 8/2006 | Wendel et al. |
| 2006/0229670 A1 | 10/2006 | Bates |
| 2006/0241579 A1 | 10/2006 | Kawaura et al. |
| 2006/0259047 A1 | 11/2006 | Hathaway et al. |
| 2007/0225748 A1 | 9/2007 | Park et al. |
| 2007/0225755 A1 | 9/2007 | Preinitz et al. |
| 2007/0225757 A1 | 9/2007 | Preinitz et al. |
| 2007/0225758 A1 | 9/2007 | Preinitz et al. |
| 2007/0276435 A1 | 11/2007 | Yassinzadeh et al. |
| 2007/0276470 A1 | 11/2007 | Tenne |
| 2008/0004653 A1 | 1/2008 | Sherman et al. |
| 2008/0058862 A1 | 3/2008 | Khosravi et al. |
| 2008/0065150 A1 | 3/2008 | Drasler et al. |
| 2008/0082122 A1 | 4/2008 | Khosravi et al. |
| 2008/0097521 A1 | 4/2008 | Khosravi et al. |
| 2008/0154303 A1 | 6/2008 | Yassinzadeh |
| 2008/0161849 A1 | 7/2008 | Cates et al. |
| 2008/0208225 A1 | 8/2008 | Seibold et al. |
| 2008/0208226 A1 | 8/2008 | Seibold et al. |
| 2008/0221615 A1 | 9/2008 | Ginn et al. |
| 2008/0312679 A1 | 12/2008 | Hardert et al. |
| 2008/0312683 A1 | 12/2008 | Drasler et al. |
| 2008/0319403 A1 | 12/2008 | Nair et al. |
| 2009/0004653 A1 | 1/2009 | Yan et al. |
| 2009/0012596 A1 | 1/2009 | Kocur et al. |
| 2009/0030450 A1 | 1/2009 | Preinitz et al. |
| 2009/0036919 A1 | 2/2009 | Preinitz et al. |
| 2009/0036920 A1 | 2/2009 | Preinitz et al. |
| 2009/0088591 A1 | 4/2009 | Bosch et al. |
| 2009/0088793 A1 | 4/2009 | Bagaoisan et al. |
| 2009/0088794 A1 | 4/2009 | LaFontaine |
| 2009/0125056 A1 | 5/2009 | Buchbinder et al. |
| 2009/0143815 A1 | 6/2009 | Eidenschink et al. |
| 2009/0143817 A1 | 6/2009 | Akerfeldt |
| 2009/0240321 A1 | 9/2009 | Davidson et al. |
| 2009/0254173 A1 | 10/2009 | Jang |
| 2009/0264821 A1 | 10/2009 | Mafi et al. |
| 2009/0275978 A1 | 11/2009 | Yassinzadeh |
| 2010/0030259 A1 | 2/2010 | Pavcnik et al. |
| 2010/0179583 A1 | 7/2010 | Carpenter et al. |
| 2010/0286725 A1 | 11/2010 | Benjamin et al. |
| 2011/0087270 A1 | 4/2011 | Penner et al. |
| 2011/0106131 A1 | 5/2011 | Argentine |
| 2011/0213410 A1 | 9/2011 | Ginn et al. |
| 2011/0213411 A1 | 9/2011 | Ginn et al. |
| 2011/0213412 A1 | 9/2011 | Ginn et al. |
| 2011/0213449 A1 | 9/2011 | Ginn et al. |
| 2011/0288580 A1 | 11/2011 | Ginn et al. |
| 2011/0295316 A1 | 12/2011 | Ginn et al. |
| 2011/0307006 A1 | 12/2011 | Murphy |
| 2012/0065668 A1 | 3/2012 | Ginn et al. |
| 2012/0083829 A1 | 4/2012 | Ginn et al. |
| 2012/0253387 A1 | 10/2012 | Teichman et al. |
| 2015/0094759 A1 | 4/2015 | Wolinsky et al. |

FOREIGN PATENT DOCUMENTS

| | | |
|---|---|---|
| EP | 1057459 | 12/2000 |
| JP | 11347130 | 12/1999 |
| JP | 2001046509 | 2/2001 |
| JP | 2006043296 | 2/2006 |
| WO | 2004012603 | 2/2004 |
| WO | 2005041782 | 5/2005 |
| WO | 2006034114 | 3/2006 |
| WO | 2006078578 | 7/2006 |
| WO | 2008094706 | 8/2008 |
| WO | 2009025836 | 2/2009 |
| WO | 2011072053 | 6/2011 |
| WO | 2011106713 | 9/2011 |

OTHER PUBLICATIONS

PCT International Preliminary Report on Patentability dated Apr. 8, 2015 for PCT/US2014/046556.

\* cited by examiner

LONGITUDINAL AXIS

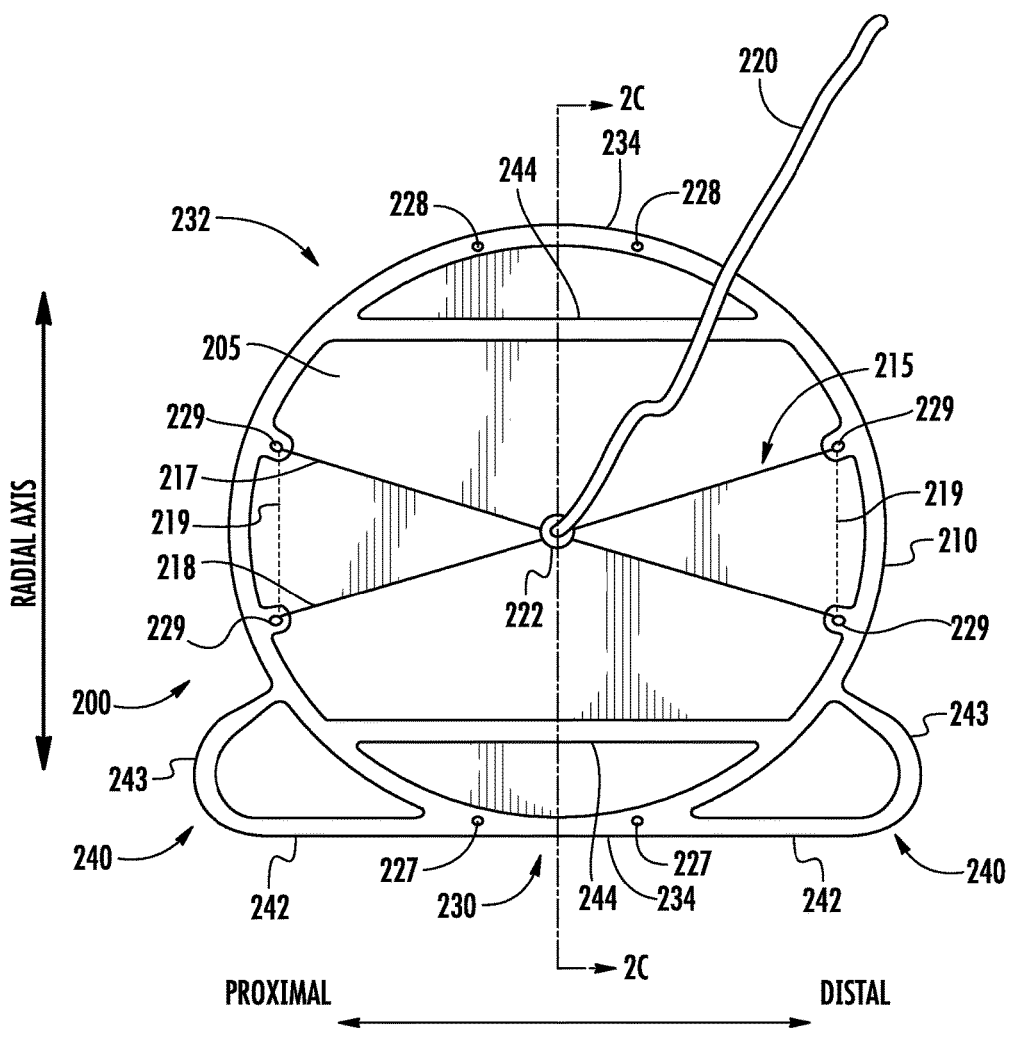
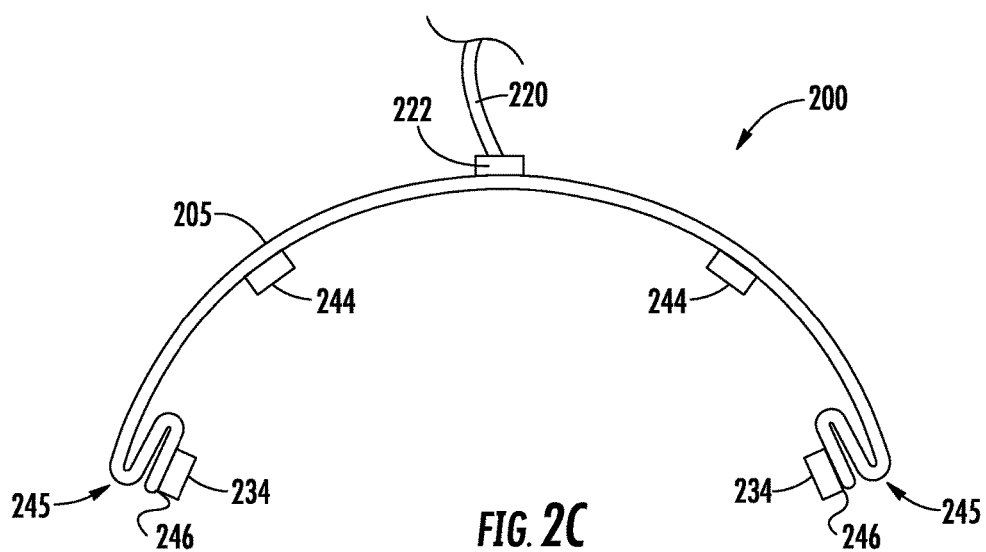

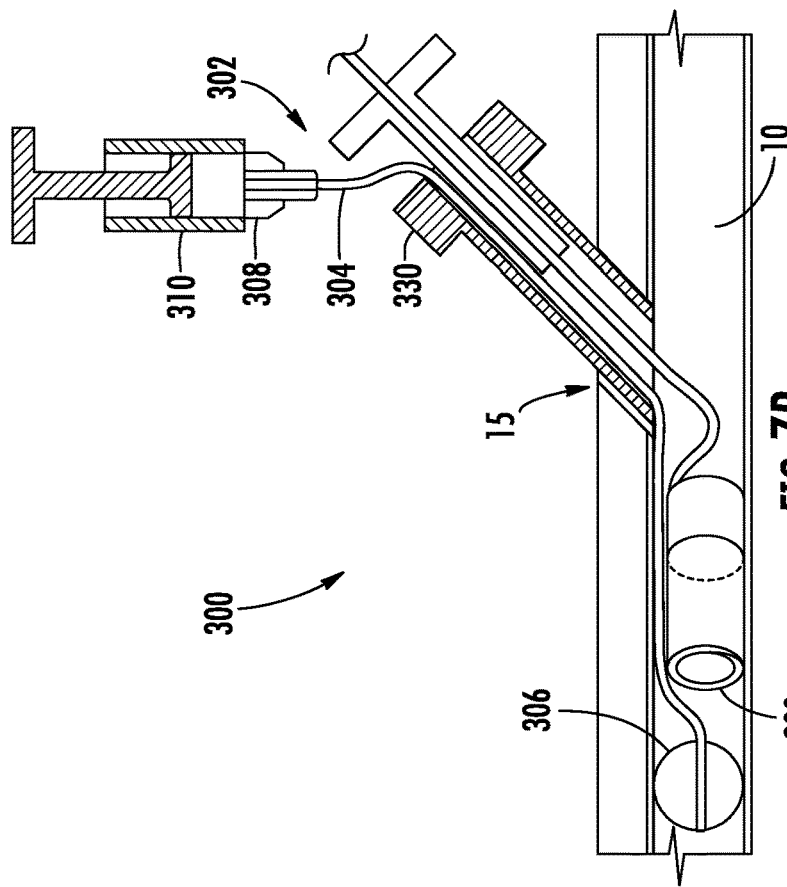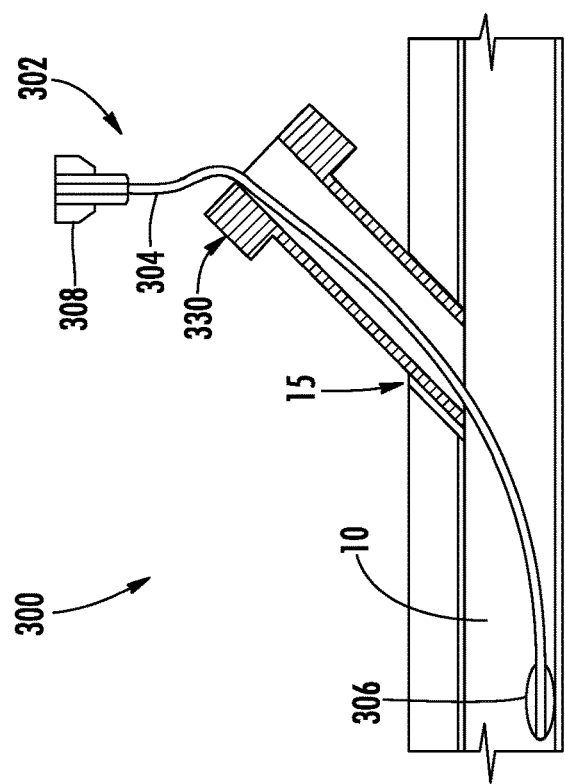

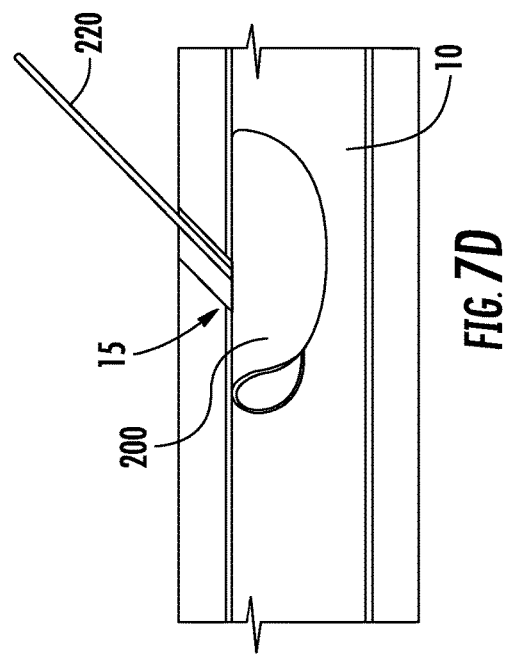
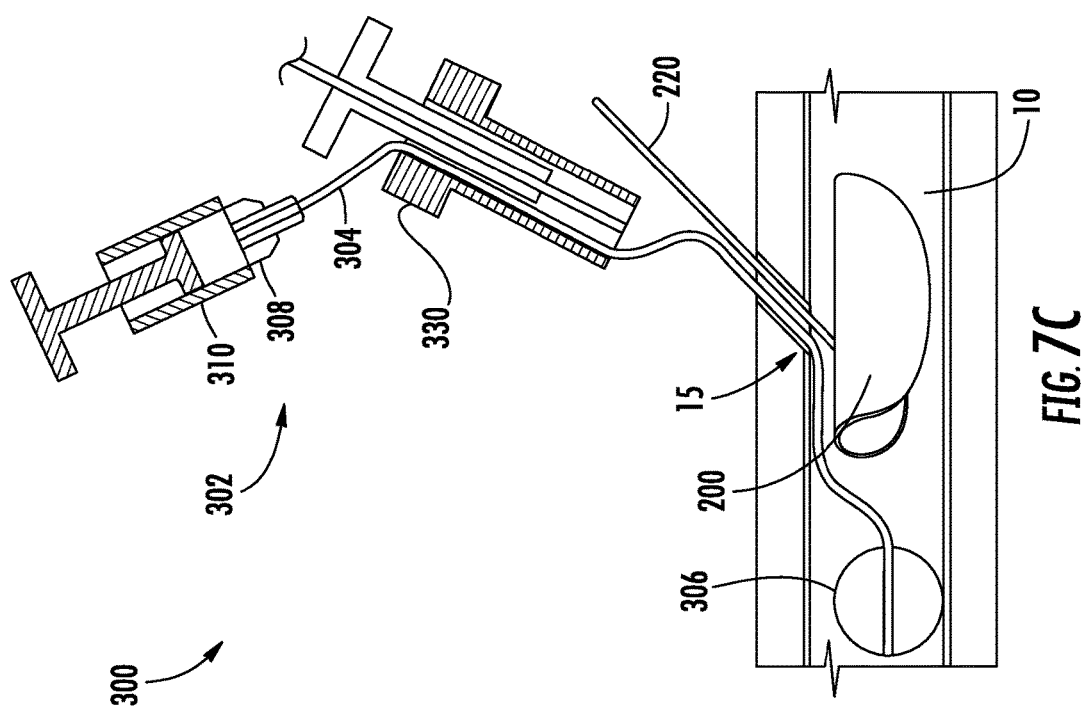

VASCULATURE CLOSURE DEVICES AND METHODS

CROSS-REFERENCE TO RELATED APPLICATIONS

This application is a U.S. national stage application of International Application Number PCT/US2014/046556, filed on Jul. 14, 2014, which claims the benefit of U.S. Provisional Application No. 61/846,419, filed on Jul. 15, 2013, and U.S. Provisional Application No. 61/978,374, filed on Apr. 11, 2014, both of which are incorporated herein by reference in their entirety.

BACKGROUND

This disclosure relates generally to the field of implantable medical devices and treatment methods, and more particularly to vasculature devices and methods for closing openings in vessel walls.

During certain types of vascular surgery, catheters are inserted through an incision in the skin and underlying tissue to access an artery, such as the femoral artery, as one example. After the surgical procedure is completed and the catheter is removed from the patient, the access hole must be closed. This is quite difficult, not only because of the high blood pressure in the artery, but also because there are many layers of tissue that must be penetrated to reach the femoral artery.

Physicians currently use a number of methods to close the artery access hole, such as localized compression, sutures, collagen plugs, adhesives, gels, foams, and/or other similar materials. To provide localized compression, the physician presses down against the vessel to allow the artery access hole to naturally clot. This method, however, can take half an hour or more, and requires the patient to remain immobilized for at least that period of time and be subsequently kept in the hospital for observation. In addition, this procedure increases the potential for clots at the puncture site to become dislodged. Moreover, the amount of time necessary for the compression can be significantly greater, depending upon how much heparin, glycoprotein IIb/IIA antagonists, or other anti-clotting agents were used during the procedure. Sutures, collagen plugs, adhesives, gels, and foams may have procedure variability, may require time to close the vessel, may have negative cost factors, may necessitate a possibly complicated deployment process, and may necessitate a separate deployment device.

For newer endovascular procedures, such as abdominal or thoracic aortic aneurysm repair, percutaneous valve replacement and repair, or cardiac ablation, which use large bore delivery systems typically in the range of 8-25 Fr, existing closure methods are suboptimal.

Certain devices and methods have been developed for closing openings in vessel walls. For example, U.S. Patent Application Publication No. 2011/0087270 to Penner et al. provides various examples of vasculature closure devices and methods for deploying and performing treatment using the same.

There remains a need for improved vasculature closure devices and methods for deploying and performing treatment using the same. It would, therefore, be advantageous to provide a vasculature closure device (VCD) that would more quickly and effectively close openings (e.g., punctures) in vessel walls. Such a device would advantageously avoid, or at least substantially reduce, the aforementioned time and expense of applying manual pressure to the opening, simplify the steps required to close the opening, avoid widening of the opening, and more effectively retain the closure device in the vessel. A more effective, safer, and easier to deliver closure device may also be beneficial for smaller sheath accesses, such as those used for cardiac catheterization (e.g., usually 4-8 Fr).

BRIEF SUMMARY

Vasculature closure devices and systems and methods for their use are provided. According to one aspect, a vasculature closure device is provided. In one or more embodiments, the vasculature closure device includes an expandable support frame deployable within a vessel, and a sealing membrane at least partially supported by the support frame. Upon expanding the support frame within the vessel, the device is configured to intraluminally position the sealing membrane against a puncture site existing in a wall of the vessel. The sealing membrane includes an area of excess membrane configured to facilitate coupling of the sealing membrane to the wall of the vessel.

In other embodiments, the vasculature closure device includes an expandable support frame deployable within a vessel, a sealing membrane at least partially supported by the support frame, and a cross-member support extending across at least a portion of the sealing membrane. Upon expanding the support frame within the vessel, the device is configured to intraluminally position the sealing membrane against a puncture site existing in a wall of the vessel. The cross-member support includes a pair of longitudinal wire segments extending between opposite sides of the support frame.

In further embodiments, the vasculature closure device includes an expandable support frame deployable within a vessel, a sealing membrane at least partially supported by the support frame, and a cross-member support extending across at least a portion of the sealing membrane. Upon expanding the support frame within the vessel, the device is configured to intraluminally position the sealing membrane against a puncture site existing in a wall of the vessel. The support frame includes a pair of longitudinal supports extending across at least a portion of the sealing membrane. The cross-member support includes a pair of radial wire segments extending between the pair of longitudinal supports.

In still other embodiments, the vasculature closure device includes an expandable support frame deployable within a vessel, a sealing membrane at least partially supported by the support frame, and a support patch extending along a portion of the sealing membrane. Upon expanding the support frame within the vessel, the device is configured to intraluminally position the sealing membrane against a puncture site existing in a wall of the vessel. The support patch is configured to increase a strength and a pressure resistance of a portion of the sealing membrane positioned over the puncture site.

According to another aspect, a method for sealing a puncture site in a vessel wall of a patient is provided. In one or more embodiments, the method includes deploying a balloon catheter through the puncture site and into the vessel, deploying a vasculature closure device through the puncture site and into the vessel, and securing at least a portion of the vasculature closure device against the puncture site for sealing thereabout.

BRIEF DESCRIPTION OF THE DRAWINGS

FIG. 2B is a top view of an example VCD according to one or more embodiments of the disclosure.

FIG. 2C is a cross-sectional end view of an example VCD according to one or more embodiments of the disclosure, taken along line 2C-2C in FIG. 2B.

FIGS. 7A-7D are partial cross-sectional side views of a delivery system and stages of delivering and securing an example VCD within a vessel according to one or more embodiments of the disclosure.

DETAILED DESCRIPTION

Figure 1:
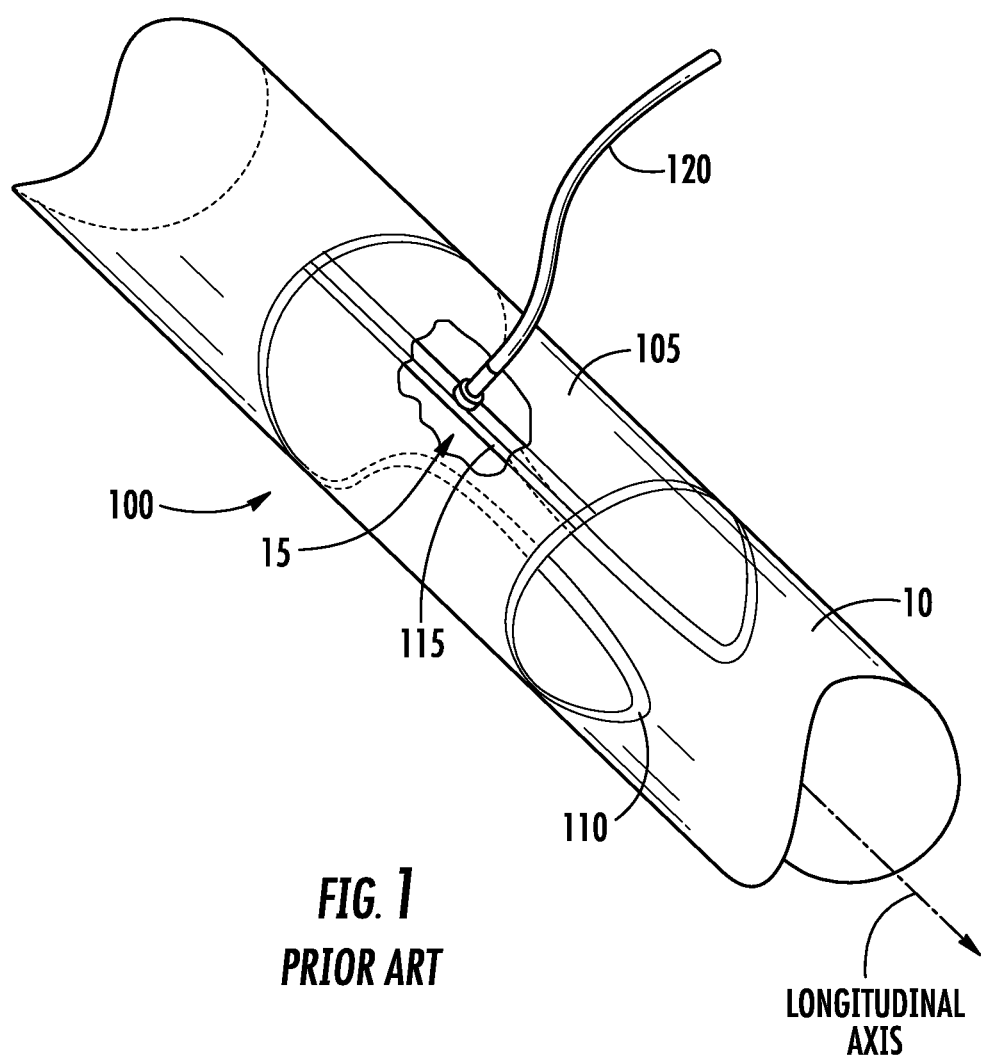
FIG. 1 is a perspective view of a prior art vasculature closure device (VCD) according to one or more embodiments implanted intraluminally within a vessel.

Vasculature closure devices (VCDs) and systems and methods for their use are provided to address some or all of the above-described needs. In particular, VCDs, systems, and methods that quickly and effectively close openings in vessel walls have been developed. Such VCDs, systems, and methods advantageously may avoid, or at least substantially reduce, the time and expense of applying manual pressure to an opening, simplify the steps required to close the opening, avoid widening of the opening, and more effectively retain the VCD in the vessel.

In certain embodiments, the VCD is configured to deform and couple to the vessel wall of a vessel having a significantly non-circular shape to effectively close an opening in the vessel wall. In particular, the VCD advantageously may include a sealing membrane having an area of excess membrane that allows the sealing membrane to extend to facilitate coupling to the vessel wall. In certain embodiments, the VCD is configured to resist undesirable deformation, weakening, or failure of the sealing membrane, particularly along the portion of the sealing membrane to be positioned over the opening in the vessel wall. In particular, the VCD advantageously may include a cross-member support extending across at least a portion of the sealing membrane and configured to increase the sealing membrane's resistance to deformation, such that the sealing membrane may withstand a pressure difference thereacross during use of the VCD. Additionally or alternatively, the VCD advantageously may include a patch extending along a portion of the sealing membrane and configured to increase the strength and pressure resistance of the portion of the sealing membrane to be positioned over the opening in the vessel wall.

In certain embodiments, the system and method for using the VCD eliminate the need for creating an additional access point in the vessel for inserting and manipulating a mechanism to control bleeding during deployment of the VCD. In particular, the system advantageously may include a balloon catheter configured to be deployed through the opening in the vessel wall to be closed by the VCD, and the method advantageously may include deploying the balloon catheter through the opening prior to deployment of the VCD therethough to control bleeding.

A VCD, according to various embodiments described herein, includes at least one sealing membrane and at least one support frame attached to, integrated with, or otherwise supporting the sealing membrane. The support frame is utilized to expand the sealing membrane from a collapsed configuration to an expanded configuration when deployed within a vessel. The support frame may be configured such that it expands enough to force the sealing membrane to move into a position against a vessel puncture. The pressure exerted by the support frame may vary but is effective to at least partially maintain the VCD at the desired position within the vessel and to at least partially press the sealing membrane against the vessel puncture. Upon positioning the VCD and exerting pressure by the sealing membrane against the vessel puncture, blood leakage is prevented or significantly reduced, and hemostasis and healing are promoted. In some instances, the sealing membrane of the VCD may significantly reduce blood leakage from the vessel puncture, while complete hemostasis is achieved by a thrombus formed on or around the sealing membrane against the puncture. Thrombus forming capabilities may be enhanced by providing thrombus promoting materials on the sealing membrane and/or a tether, positioning tab, or anchoring tab of the VCD. The VCD may be left in the secured position within the vessel for essentially any period of time, which may be indefinitely in certain embodiments.

According to various embodiments, portions of the VCD are biodegradable, bioabsorbable, and/or bioerodable (collectively referred to herein as "biodegradable" unless expressly stated otherwise), such that after a period of time portions degrade, absorb, and/or erode. For example, at least the sealing membrane, and in some embodiments the support frame or portions thereof and/or a tether, positioning tab, or anchoring tab of the VCD, may degrade, dissolve, or become absorbed after a preselected period of time, minimizing the components remaining within the vessel over time. This may simplify subsequent access at or near the vessel puncture site and reduces potential long-term complications. The shape, configuration, and composition of the various components of the VCD, and the systems and methods for delivering the same, may be embodied in a number of manners, representative examples of which are described below.

The VCD described herein may be used to close punctures or penetrations in vessels in human or other animals (e.g., mammalian). Such an animal may be referred to herein as a patient. As used herein, the term "vessel" refers to arteries, veins, other vascular lumens for carrying blood or lymph, or other body lumens, such as, but not limited to, body lumens of the gastrointestinal system (e.g., the esophagus, the stomach, the small intestine, or the large intestine), the airway system (e.g., the trachea, the bronchus, or the bronchioles), the urinary system (e.g., the bladder, the ureters, or the urethra), or the cerebrospinal system (e.g., subarachnoid space or the ventricular system around and/or inside the brain and/or the spinal cord). The VCD may be dimensioned for effective use with a variety of vessel anatomies and sizes in adult and pediatric patients, as well as with punctures at a variety of vessel sites within the patient. It is envisioned that the VCD may be adapted for use in closing punctures in other body lumens in conjunction with various surgical procedures. For example, in one other embodiment, the VCD may be adapted for use to close lumen punctures during natural orifice transluminal endoscopic surgery or to close a lumbar puncture.

Vasculature Closure Devices

Referring to the figures, FIG. 1 depicts a prior art VCD 100 according to one or more embodiments, the VCD 100 implanted intraluminally within a patient's vessel 10 and positioned and secured therein to at least temporarily seal a target area at or near a vessel puncture site 15 (which is interchangeably referred to herein as the "access hole," "access site," "vessel puncture," "puncture hole," "puncture site," or other similar variations thereof) existing through a wall of the vessel 10. The VCD 100 includes a sealing membrane 105 and an expandable support frame 110 providing shape and support to the sealing membrane 105 along at least a portion of the sealing membrane's 105 periphery. In other words, the sealing membrane 105 is at least partially supported by the support frame 110.

The support frame 110, and thus generally the VCD 100, is configured to expand from a collapsed configuration into an expanded configuration within the vessel 10. Upon expanding the support frame 110, the VCD 100 is configured to intraluminally position the sealing membrane 105 against the puncture site 15 to at least partially seal the puncture site 15. In some embodiments, as is shown in FIG. 1, the sealing membrane 105 and the support frame 110, and thus generally the VCD 100, may be formed in any shape configured for rolling and unrolling along a longitudinal axis generally aligned with and extending along the length of the lumen of the vessel 10 when implanted. The expansion of the VCD 100 thus may be in a radial direction i.e., perpendicular to the longitudinal axis, within the lumen of the vessel 10. For example, the VCD 100 may have a simple form that is similar in configuration to a sheet that can roll or unroll, or a tube that is slit entirely along its longitudinal axis. However, the VCD 100 may have any other shape that can be collapsed and then expanded within a vessel to promote securement of the VCD 100 therein.

The VCD 100 also includes a cross-member support 115 extending across at least a portion of the sealing membrane 105. The cross-member support 115, due to its rigidity or at least partial rigidity, and/or tension provided by the peripheral support frame 110, provides structural and shape support to the sealing membrane 105. In some embodiments, the cross-member support 115 is more rigid than the sealing membrane 105. Upon expanding the support frame 110, the cross-member support 115 is configured to maintain the sealing membrane 105 against the puncture site 15, as is shown in FIG. 1. In other words, the cross-member support 115 may support the sealing membrane 105 to avoid sagging where the sealing membrane 105 bridges the puncture site 15, thus improving the seal created therebetween. In some embodiments, the cross-member support 115 extends between opposite sides of the support frame 110 and supports the sealing membrane 105 at or near a center of the sealing membrane 105 to avoid sagging at the puncture site 15. The cross-member support 115 also is configured to increase longitudinal rigidity of the VCD 100 during deployment into the vessel 10. In this manner, the cross-member support 115 may provide the longitudinal rigidity necessary for rolling the VCD 100 along the longitudinal axis and maintaining the VCD 100 in the collapsed configuration for deployment. In such embodiments, the VCD 100 may be configured for rolling and unrolling along a longitudinal axis defined by the cross-member support 115.

As is shown in FIG. 1, the VCD 100 further includes a tether, positioning tab, or anchoring tab 120 extending from the sealing membrane 105, the support frame 110, and/or the cross-member support 115. Specifically, the tether 120 is attached to at least one of the sealing membrane 105, the support frame 110, and/or the cross-member support 115, according to certain embodiments. Upon deployment of the VCD 100 within the vessel 10, the tether 120 extends out of and away from the puncture site 15. In this manner, the tether 120 may be pulled through and away from the puncture site 15 to position the sealing membrane 105 and the support frame 110 against an inner surface of the wall of the vessel 10 about the puncture site 15. Further, the tether 120 may facilitate intraluminal positioning or centering of the VCD 100 across the puncture site 15, as the VCD 100 may tend to migrate in a downstream direction (e.g., due to intravascular blood flow) toward a distal portion of the vessel 10 until the tether 120 abuts an edge of the vessel puncture 15. According to some embodiments, upon positioning the VCD 100 within the vessel 10, the free end portion of the tether 120 may be fixed to the patient, typically while the tether 120 is in tension. For example, the free end portion of the tether 120 may be affixed (e.g., sutured, glued, hooked, held by an elastic retaining means, etc.) to the patient's epidermis, dermis, sub-dermal layer, adipose layer, or muscle tissue at or near the vessel access site (e.g., at or near the initial incision created for access to the vessel).

It is appreciated that FIG. 1 is provided to depict one orientation of an embodiment of the VCD 100 within a vessel 10, and that any VCD according to the various embodiments described herein may be similarly positioned intraluminally to secure or otherwise retain a sealing membrane against a puncture site. These embodiments are described in more detail with reference to the figures.

Figure 2A:
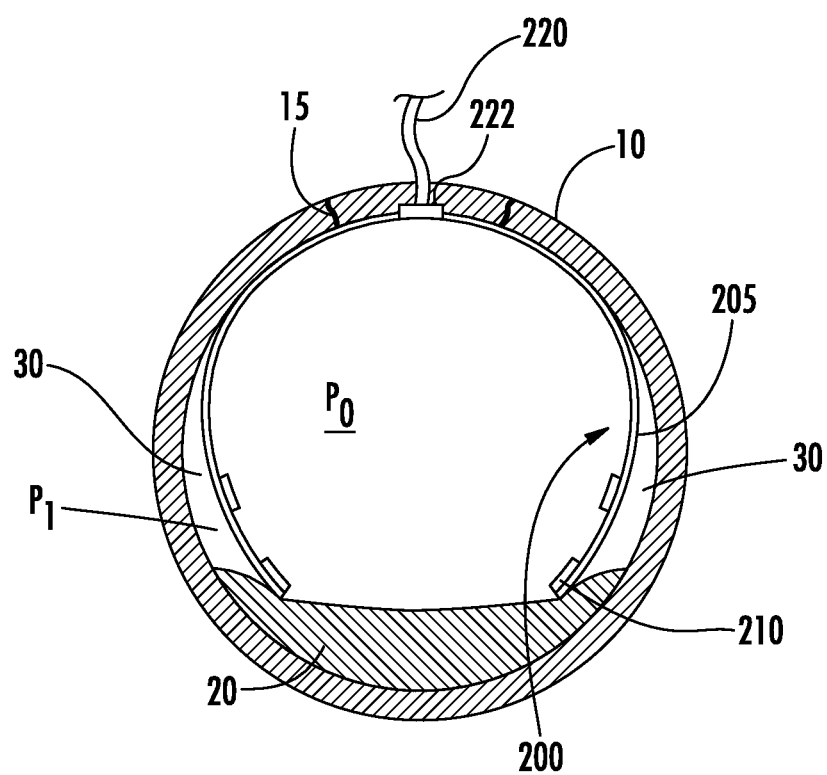
FIG. 2A is a cross-sectional end view of an example VCD according to one or more embodiments of the disclosure implanted intraluminally within a vessel.

FIG. 2A depicts an example VCD 200 according to one or more embodiments of the disclosure, the VCD 200 implanted intraluminally within a patient's vessel 10 to facilitate hemostasis and closure of a vessel puncture 15. FIG. 2B depicts the VCD 200 according to one or more embodiments of the disclosure (the VCD 200 is shown in FIG. 2B in a flat, fully unrolled configuration for illustration purposes only). The VCD 200 is similar to the VCD 100 depicted in and described with reference to FIG. 1, although certain differences in structure and function are described herein below. The VCD 200 includes a sealing membrane 205 and an expandable support frame 210 providing shape and support to the sealing membrane 205 along at least a portion of the sealing membrane's 205 periphery. In other words, the sealing membrane 205 is at least partially supported by the support frame 210.

The support frame 210, and thus generally the VCD 200, is configured to expand from a collapsed configuration into an expanded configuration within the vessel 10. Upon expanding the support frame 210, the VCD 200 is configured to intraluminally position the sealing membrane 205 against a vessel puncture site to at least partially seal the vessel puncture 15. In some embodiments, the sealing membrane 205 and the support frame 210, and thus generally the VCD 200, are formed in any shape configured for rolling and unrolling along a longitudinal axis generally aligned with and extending along the length of the lumen of the vessel 10 when implanted. Specifically, the support frame 210 may be formed in a shape configured for rolling into the collapsed configuration and unrolling into the expanded configuration. The expansion of the VCD 200 thus may be in a radial direction i.e., perpendicular to the longitudinal axis, within the lumen of the vessel 10. For example, as is shown in FIGS. 2A and 2B, the VCD 200 may have a simple form that is similar in configuration to a sheet that can roll or unroll. However, the VCD 200 may have any other shape that can be collapsed and then expanded within a vessel to promote securement of the VCD 200 therein.

The VCD 200 also includes a cross-member support 215 extending across at least a portion of the sealing membrane 205. In some embodiments, the cross-member support 215 extends between opposite sides of the support frame 210. The cross-member support 215, due to its relative rigidity and/or tension provided by the peripheral support frame 210, may provide structural and shape support to the sealing membrane 205. The cross-member support 215 may be more rigid than the sealing membrane 205, or the cross-member support 215 may be less rigid than the sealing membrane. In some embodiments, upon expanding the support frame 210, the cross-member support 215 is configured to maintain the sealing membrane 205 against the vessel puncture site 15. Specifically, the cross-member support 215 may support the sealing membrane 205 to avoid sagging where the sealing membrane 205 bridges the vessel puncture site 15, thus improving the seal created therebetween. In some embodiments, upon expanding the support frame 210, the cross-member support 215 is configured to prevent excessive displacement of the sealing membrane 205, such as displacement into and/or through the vessel puncture site 15, as well as excessive stress generated in the sealing membrane 205 due to blood pressure within the vessel 10. In some embodiments, the cross-member support 215 also is configured to increase longitudinal rigidity of the VCD 200 during deployment into the vessel 10. In this manner, the cross-member support 215 may provide the longitudinal rigidity necessary for rolling the VCD 200 along the longitudinal axis and maintaining the VCD 200 in the collapsed configuration for deployment. In such embodiments, the VCD 200 may be configured for rolling and unrolling along a longitudinal axis defined by the cross-member support 215. In other embodiments, features other than the cross-member support 215 are configured to increase longitudinal rigidity of the VCD 200 during deployment into the vessel 10, as may be described herein below.

In certain embodiments, the cross-member support 215 is formed separately from and attached to the support frame 210. As is shown in FIG. 2B, the cross-member support 215 is attached to opposite sides of the support frame 210. In some embodiments, the cross-member support 215 extends over the sealing membrane 205 and is configured to be positioned between the sealing membrane 205 and the wall of the vessel 10. In this manner, the cross-member support 215 may be particularly configured to prevent excessive displacement of the sealing membrane 205, such as displacement into and/or through the vessel puncture site 15. In other embodiments, the cross-member support 215 extends beneath the sealing membrane 205 and is configured to be positioned between the sealing membrane 205 and a flow of blood through the vessel 10. In such embodiments, the cross-member support 215 may be attached to the sealing membrane 205 and thus may be configured to prevent excessive displacement of the sealing membrane 205, such as displacement into and/or through the vessel puncture site 15. As is shown in FIG. 2B, the cross-member support 215 is in the form of a flexible wire. In some embodiments, the flexible wire is formed of a surgical suture material. Examples of suitable materials of construction of the flexible wire include polymeric materials, such as PEEK, fluorocarbon polymers, polyamides, polyimides, polyethylenes, polypropylenes, or similar polymers and copolymers. In some embodiments, the flexible wire is formed of a biodegradable material. Examples of suitable biodegradable materials of construction of the flexible wire include PLLA, PDLA, PGA, PLGA, PDS, PCL, PGA-TMC, polygluconate, and polylactic acid-polyethylene oxide.

As is shown in FIG. 2B, the cross-member support 215 is in the form of a flexible wire including a first wire segment 217 extending between opposite sides of the support frame 210 and a second wire segment 218 extending between opposite sides of the support frame 210. As is shown, the first wire segment 217 and the second wire segment 218 define an X-shape of the cross-member support 215, such that the first wire segment 217 and the second wire segment 218 are configured to distribute forces applied to the cross-member support 215. In some embodiments, the first wire segment 217 and the second wire segment 218 are formed of a single flexible wire and are connected to one another by one or more additional wire segments 219, as is shown by dashed lines in FIG. 2B. In this manner, the single flexible wire includes the first wire segment 217, the second wire segment 218, and the additional wire segments 219. In other embodiments, the first wire segment 217 and the second wire segment 218 are formed of separate wires. In some embodiments, the cross-member support 215 extends over the sealing membrane 205 and is configured to be positioned between the sealing membrane 205 and the wall of the vessel 10. In other embodiments, the cross-member support 215 extends beneath the sealing membrane 205 and is configured to be positioned between the sealing membrane 205 and a flow of blood through the vessel 10. In still other embodiments, a portion of the cross-member support 215 extends over the sealing membrane 205 and is configured to be positioned between the sealing membrane 205 and the wall of the vessel 10, and another portion of the cross-member support 215 extends beneath the sealing membrane 205 and is configured to be positioned between the sealing membrane 205 and a flow of blood through the vessel 10. For example, the first wire segment 217 and the second wire segment 218 may extend over the sealing membrane 205, and the additional wire segments 219 may extend beneath the sealing membrane 205. In some embodiments, the cross-member support 215 is coupled to the sealing membrane 205 at an intermediate portion of the cross-member support 215. In other words, the cross-member support 215 is coupled to the sealing membrane 205 at a portion between the ends of the cross-member support 215. In some embodiments, the intermediate portion of the cross-member support 215 is coupled to the sealing membrane 205 by a glue or solvent along one or more areas of the intermediate portion.

As is shown in FIG. 2B, the VCD 200 further includes a tether, positioning tab, or anchoring tab 220 attached to the cross-member support 215. Specifically, the tether 220 may be attached to the cross-member support 215 at a securing point 222 at a center of the X-shape of the cross-member support 215. In this manner, the first wire segment 217 and the second wire segment 218 may be configured to distribute pulling forces applied to the cross-member support 215 via the tether 220 to reduce bending of the support frame 210. Accordingly, greater pulling forces may be applied during positioning of the VCD 200 within the vessel before significant bending or deformation of the support frame 210 occurs. The securing point 222 may be at about the center of the longitudinal axis of the VCD 200. Alternatively, the securing point 222 may be at about 1 mm to about 6 mm proximal to or at about 1 mm to about 6 mm distal to the center of the longitudinal axis of the VCD 200. In some embodiments, the tether 220 is formed of a flexible wire, such as the same type of flexible wire as the cross-member support 215. In some embodiments, the tether 220 and the cross-member support 215 are formed of a single flexible wire. In this manner, the single flexible wire includes the first wire segment 217, the second wire segment 218, the additional wire segments 219, and the tether 220. In such embodiments, the securing point 222 may include a knot or other securing mechanism for arranging the tether 220 relative to the cross-member support 215.

Upon deployment of the VCD 200 within the vessel 10, the tether 220 extends out of and away from the vessel puncture site 15, as is shown in FIG. 2A. In this manner, the tether 220 may be pulled through and away from the vessel puncture site 15 to position the sealing membrane 205 and the support frame 210 against an inner surface of the wall of the vessel 10 about the vessel puncture site 15. Further, the tether 220 may facilitate intraluminal positioning or centering of the VCD 200 across the vessel puncture site 15, as the VCD 200 may tend to migrate in a downstream direction toward a distal portion of the vessel 10 until the tether 220 abuts an edge of the vessel puncture 15. According to some embodiments, upon positioning the VCD 200 within the vessel 10, the free end portion of the tether 220 may be affixed to the patient.

As is shown in FIG. 2B, the support frame 210 is formed as a peripheral support frame defining an oval shape, although the peripheral support frame may define a circular shape in other embodiments. The sealing membrane 205 may define an outer edge about its periphery, and at least a portion of the support frame 210 may be positioned along the outer edge of the sealing membrane 205. In some embodiments, the outer edge of the sealing membrane 205 extends beyond the outer edges of the support frame 210. The sealing membrane 205 may be attached to the support frame 210 using glue, solvent adhesion, laser welding, ultrasonic welding, thermal welding, or any other means of attachment. In some embodiments, the sealing membrane 205 includes a plurality of tabs extending about the outer edge, and the sealing membrane 205 is attached to the support frame 210 by the plurality of tabs. Specifically, each of the tabs may wrap around a portion of the support frame 210 and be bonded to the sealing membrane 205 or wrapped around the support frame 210 and bonded to itself. In other embodiments, as is shown in FIG. 2B, the support frame 210 defines a plurality of holes 227, 228 for attaching the sealing membrane 205 to the support frame 210. Specifically, the sealing membrane 205 may be attached to the support frame 210 by a plurality of anchors extending through the plurality of holes 227, 228. The anchors may be formed of a glue or adhesive used to fill the holes 227, 228 until reaching the membrane 205, such that the cured glue or adhesive forms a stud-like shape extending through the holes 227, 228 and holding the sealing membrane 205 to the support frame 210. Alternatively, the anchors may be formed of the same material as the sealing membrane 205, for example by casting, such that the material forms a stud-like shape extending through the holes 227, 228 and holding the sealing membrane 205 to the support frame 210. Further, the anchors may be formed as a wire, such as a surgical suture material, or a rivet type fastener extending through the plurality of holes 227, 228. In other embodiments, the sealing membrane 205 is attached to the support frame 210 via a combination of the plurality of tabs of the sealing membrane 205 and the plurality of anchors extending through the plurality of holes 227, 228 of the support frame 210. In still other embodiments, the support frame 210 is integrated with the sealing membrane 205 during manufacturing. The integrated configuration may be formed, for example, by depositing or casting an initial layer of the sealing membrane 205, placing the support frame 210 onto the initial layer of the sealing membrane 205, and then depositing or casting a second layer of the sealing membrane 205 onto the initial layer and the support frame 210, such that the support frame 210 is embedded within the sealing membrane 205. In some embodiments, as is shown in FIG. 2B, the support frame 210 defines a plurality of holes 229 for attaching the cross-member support 215 to the support frame 210.

As discussed above, the support frame 210 is configured to expand from a collapsed configuration into an expanded configuration within the vessel 10. Specifically, the support frame 210 may be configured to expand from the collapsed configuration having a first radius of curvature into the expanded configuration having a second radius of curvature greater than the first radius of curvature. In some embodiments, the support frame 210 is configured to expand into the expanded configuration having a radius of curvature greater than a radius of curvature of the vessel 10. In some embodiments, the support frame 210 is formed of a self-expandable or pre-shaped material having a pre-shaped expanded configuration, such that the support frame 210 tends to assume the pre-shaped expanded configuration absent the application of external forces to the support frame 210. In this manner, the support frame 210 may be configured to self-expand from the collapsed configuration into the pre-shaped expanded configuration within the vessel 10 upon deployment or release of the VCD 200 from a containment mechanism (and consequent release of a compressive load holding the VCD 200 in the collapsed configuration). The pre-shaped material may include a shape memory metal and/or a shape memory polymer, and the pre-shaped expanded configuration of the support frame 210 may be defined by the stable shape of the shape memory metal and/or shape memory polymer. Preferably, the support frame 210 is formed of a nickel-titanium alloy. Other elastic or super-elastic materials may be used to form the support frame 210.

As discussed above, the support frame 210 is configured for rolling into the collapsed configuration and unrolling into the expanded configuration. In some embodiments, as is shown in FIG. 2B, the support frame 210 includes a first wing 230 and a second wing 232 positioned opposite the first wing 230 at radial ends of the VCD 200. In this manner, the second wing 232 may be rolled over the first wing 230 when the support frame 210 is in the collapsed configuration. The first wing 230 and the second wing 232 each may include a frame strut 234 extending about the respective radial end of the support frame 210, as is shown. The support frame 210 also may include at least one, and preferably two, tabs or ear supports 240 extending from the first wing 230. The tabs 240 may provide multiple utilities. First, the tabs 240 may be configured to increase a longitudinal stiffness of the VCD 200 when the support frame 210 is in the collapsed configuration during delivery of the VCD 200. Specifically, in some embodiments, each of the tabs 240 includes a straight segment 242 extending along the longitudinal axis of the VCD 200, which serves as a longitudinal stiffener. Second, the tabs 240 may be configured to prevent the first wing 230 from applying pressure on the sealing membrane 205 when the support frame 210 is in the collapsed configuration. Specifically, in some embodiments, each of the tabs 240 includes a curved segment 243 configured to contact a portion of the support frame 210 that is rolled over the tabs 240 when the support frame 210 is in the collapsed configuration, such that the first wing 230 does not contact the sealing membrane 205. The curved segment 243 may be configured to contact the support frame 210 at or near the centerline of the support frame 210 (i.e., between the first wing 230 and the second wing 232). Third, the tabs 240 may be configured to apply a force to the portion of the support frame 210 that is rolled over the tabs 240 for unrolling the support frame 210 into the expanded configuration. Specifically, in some embodiments, the curved segments 243 of the tabs 240 are configured to apply an expansion force to the support frame 210 at or near the centerline of the support frame 210 such that the support frame 210 self-expands from the collapsed configuration into the pre-shaped expanded configuration. In the absence of the tabs 240, and specifically the curved segments 243 of the tabs 240, the expansion force would be applied by the first wing 230 to the sealing membrane 205, which may result in damage or unwanted deformation to the sealing membrane 205 or penetration of the first wing 230 into the sealing membrane 205 and which may significantly increase the force needed to expand the support frame 210, possibly to a level such that the support frame 210 may not be able to return to its expanded configuration upon release of the containment mechanism. In some embodiments, as is shown in FIG. 2B, the support frame 210 further includes one or more longitudinal supports 244 extending longitudinally between opposite sides of the support frame 210. The longitudinal supports 244 may be configured to increase a longitudinal rigidity of the VCD 200, particularly when the support frame 210 is in the collapsed configuration during delivery of the VCD 200 into the vessel 10. In this manner, the longitudinal supports 244 may provide the longitudinal rigidity necessary for rolling the VCD 200 along the longitudinal axis and maintaining the VCD 200 in the collapsed configuration for deployment.

As discussed above, the support frame 210 may be configured to expand from the collapsed configuration into the expanded configuration within the vessel 10 upon deployment or release of the VCD 200 from a containment mechanism (and consequent release of a compressive load holding the VCD 200 in the collapsed configuration). Upon expansion, the support frame 210 may couple the VCD 200 to the vessel wall. The sealing membrane 205 may be flexible and thus may adapt to the contour of the vessel wall due to force applied to the sealing membrane 205 by the blood pressure within the vessel 10. However, it has now been discovered that in some cases where the vessel 10 is significantly non-circular, the support frame 210 may not be able to couple to the vessel wall along certain points or areas of the support frame 210. For example, as is shown in FIG. 2A, the vessel 10, and thus the lumen defined therein, may be non-circular due to a disease or calcification 20, which may prevent the support frame 210 from coupling to the vessel wall along certain areas of the support frame 210. As a result, a gap 30 may exist between the outer surface of the sealing membrane 205 and the vessel wall. The gap 30 may be large enough to allow significant blood flow therethough, which may at least partially balance the blood pressure applied to the inner surface of the sealing membrane 205. Although the sealing membrane 205 may be substantially flexible or visco-elastic, the ability of the sealing membrane 205 to deform and the rate at which the sealing membrane 205 will deform depend highly on the force applied to the sealing membrane 205. The force is linearly proportional to the pressure difference across the sealing membrane 205. In other words, the force F applied is linearly proportional to the difference between the pressure $P_0$ along the inner surface of the sealing membrane 205 and the pressure $P_1$ along the outer surface of the sealing membrane 205 ($F \propto P_0 - P_1$). In this manner, a small pressure difference across the sealing membrane 205 will decrease its ability to deform and consequently its ability to couple to the vessel wall and seal the vessel puncture 15.

Described herein are various embodiments of the VCD 200 that allow the sealing membrane 205 to deform and couple to the vessel wall of a vessel 10 having a significantly non-circular shape. The various embodiments solve the above-described problem by including an excess membrane area of the sealing membrane 205 to provide a certain degree of "slack" therein and to allow the sealing membrane 205 to couple to the vessel wall and seal the vessel puncture 15. In some embodiments, the sealing membrane 205 is flexible and is configured to couple to the vessel wall and seal the vessel puncture 15 via a combination of deformation of the sealing membrane 205 and extension of the excess membrane area. In other embodiments, the sealing membrane 205 is substantially inflexible and is configured to couple to the vessel wall and seal the vessel puncture 15 via extension of the excess membrane area (i.e., extension of the excess membrane area is sufficient for coupling and sealing). The excess membrane area may be formed by using a sealing membrane 205 that is larger than the support frame 210 to which is it coupled. For example, the sealing membrane 205 may be longer than the support frame 210 in one or more directions, such that the excess membrane area is an area of excess membrane length in the one or more directions. The excess membrane area may be substantially evenly distributed over the full area of the sealing membrane 205, substantially randomly distributed over the area of the sealing membrane 205, or concentrated in one or more areas of the sealing membrane 205. The excess membrane area may extend along the radial axis of the VCD 200, along the longitudinal axis of the VCD 200, along both the radial axis and the longitudinal axis of the VCD 200, along parts of the circumference of the support frame 210, or along the full circumference of the support frame 210. The sealing membrane 205 may be coupled to the support frame 210 according to any of the methods described above. For example, adhesive may be used to couple the sealing membrane 205 along the circumference of the support frame 210, in one or more areas or points. In some embodiments, the holes 227, 228 in the support frame 210 are used to improve the adhesive strength. Alternatively, the sealing membrane 205 may include one or more tabs along its circumference which may by wrapped around portions of the support frame 210 and bonded to the sealing membrane 205 by an adhesive or glue.

FIGS. 2C-2F depict various embodiments of the VCD 200, showing cross-sectional end views taken along line 2C-2C of FIG. 2B in the direction of the radial axis of the VCD 200 (the VCD 200 is shown in FIGS. 2C-2F in a curved, partially unrolled configuration). In these embodiments, the sealing membrane 205 includes an area of excess membrane that allows the sealing membrane 205 to extend to facilitate coupling to the vessel wall of a vessel 10 having a significantly non-circular shape.

As is shown in FIG. 2C, the sealing membrane 205 includes one or more areas of excess membrane 245 extending along the radial axis of the VCD 200. The sealing membrane 205 is connected to the frame struts 234 of the support frame 210 at connection points 246, as is shown in detail in FIG. 3A. The one or more areas of excess membrane 245 may be folded in proximity to the frame struts 234 of the support frame 210. Other options for connecting the sealing membrane 205 to the frame struts 234 and for folding or otherwise storing the one or more areas of excess membrane 245 are shown in FIGS. 3B-3F. The one or more areas of excess membrane 245 may be formed by using a sealing membrane 205 that is larger than the support frame 210 by about 0.1 mm to about 10 mm, by about 1 mm to about 6 mm, or by about 2 mm to about 4 mm in at least one direction, such as along the radial axis, the longitudinal axis, or both the radial axis and the longitudinal axis of the VCD 200. The one or more areas of excess membrane 245 may be distributed uniformly over the VCD 200 or concentrated at one, two, or more areas of the VCD 200. In some embodiments, the one or more areas of excess membrane 245 are formed substantially only along the radial axis of the VCD 200, while in other embodiments, the one or more areas of excess membrane 245 are formed substantially only along the longitudinal axis of the VCD 200. In still other embodiments, the one or more areas of excess membrane 245 are formed along the entire perimeter of the sealing membrane 205. The one or more areas of excess membrane 245 may be formed along the perimeter of the support frame 210 or substantially along the perimeter of the support frame 210. The one or more areas of excess membrane 245 may be substantially evenly distributed over the full area of the sealing membrane 205, substantially randomly distributed over the full area of the sealing membrane 205, or concentrated in one or more areas of the sealing membrane 205.

Figure 2D:
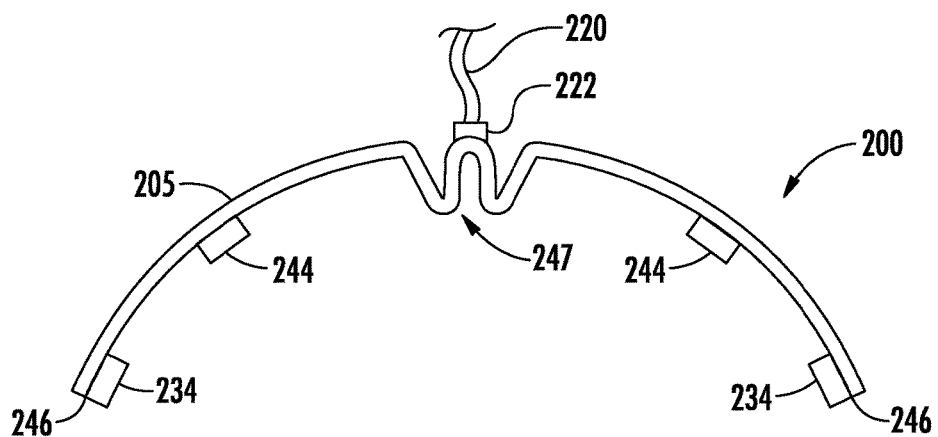
FIG. 2D is a cross-sectional end view of an example VCD according to one or more embodiments of the disclosure, similar to the view of FIG. 2C.

As is shown in FIG. 2D, the sealing membrane 205 includes an area of excess membrane 247 extending along the radial axis of the VCD 200. The area of excess membrane 247 may be formed substantially at the center of the sealing membrane 205 along the radial axis of the VCD 200. The area of excess membrane 247 may be folded, including one or more folds, as is shown. The folds may extend perpendicular to the surface defined by the sealing membrane 205. The folds may extend below the surface defined by the sealing membrane 205, above the surface defined by the sealing membrane 205, or both below and above the surface defined by the sealing membrane 205.

Figure 2E:
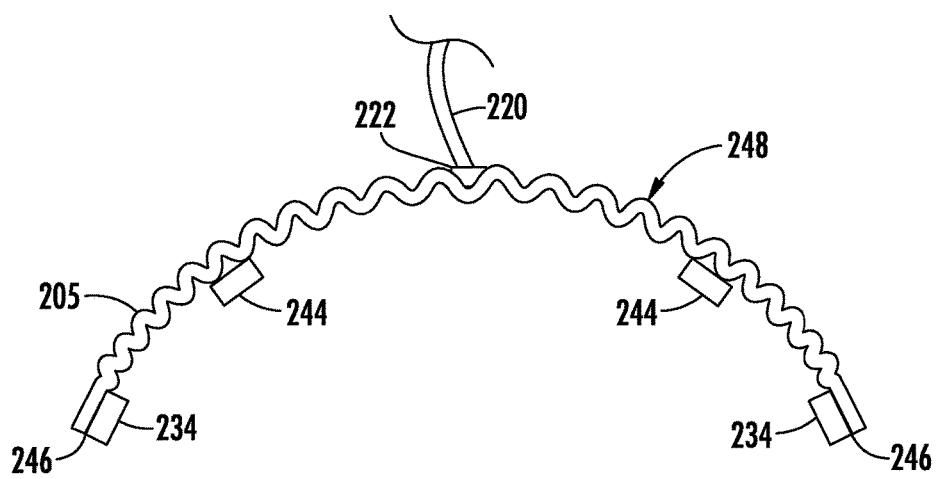
FIG. 2E is a cross-sectional end view of an example VCD according to one or more embodiments of the disclosure, similar to the view of FIG. 2C.

As is shown in FIG. 2E, the sealing membrane 205 includes an area of excess membrane 248 extending along the radial axis of the VCD 200. The area of excess membrane 248 may extend along the entire radial length of the sealing membrane 205, such that the excess membrane is distributed uniformly within the support frame 210, as is shown. The area of excess membrane 248 may be wrinkled, including a plurality of wrinkles, as is shown.

Figure 2F:
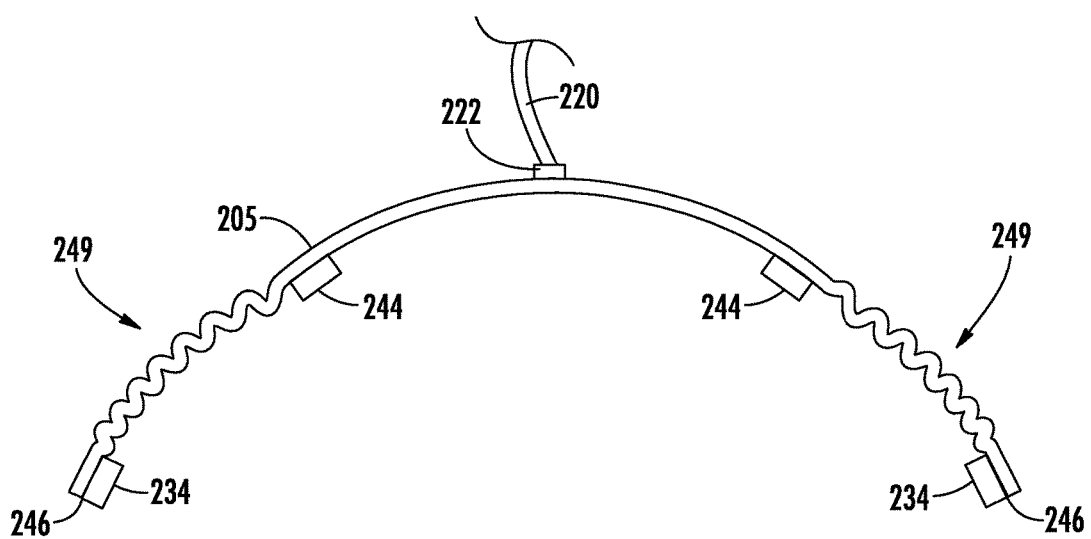
FIG. 2F is a cross-sectional end view of an example VCD according to one or more embodiments of the disclosure, similar to the view of FIG. 2C.

As is shown in FIG. 2F, the sealing membrane 205 includes a plurality of areas of excess membrane 249 extending along the radial axis of the VCD 200. Specifically, the sealing membrane 205 may include two areas of excess membrane 249 concentrated along radial ends of the sealing membrane 205 in proximity to the frame struts 234 of the support frame 210. The areas of excess membrane 249 may be folded, including one or more folds, or wrinkled, including a plurality of wrinkles, as is shown. The folds or wrinkles may extend perpendicular to the surface defined by the sealing membrane 205. The folds or wrinkles may extend below the surface defined by the sealing membrane 205, above the surface defined by the sealing membrane 205, or both below and above the surface defined by the sealing membrane 205.

FIGS. 3A-3F depict portions of various embodiments of the VCD 200, showing different connections between the sealing membrane 205 and the support frame 210 to provide the area of excess membrane 245.

Figure 3A:
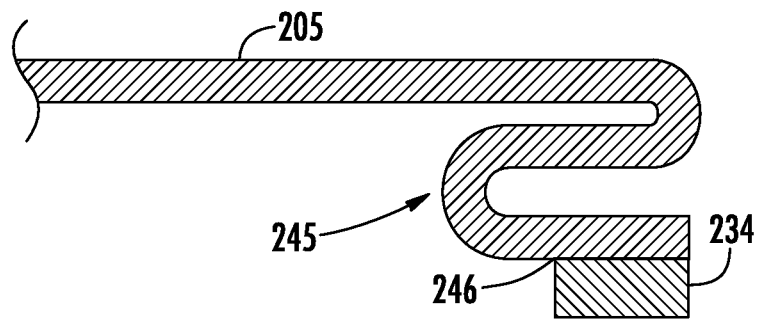
FIG. 3A is a cross-sectional end view of a portion of an example VCD according to one or more embodiments of the disclosure.

As is shown in FIG. 3A, the sealing membrane 205 is connected to the frame strut 234 of the support frame 210 at the connection point 246 using adhesive, welding, pins, staples, sutures, or any other coupling means. The sealing membrane 205 may be connected to the top side of the frame strut 234, as is shown. Alternatively, the sealing membrane 205 may be connected to the bottom side of the frame strut 234. The area of excess membrane 245 may be folded, including one or more folds, as is shown. The folds may extend parallel to the surface defined by the sealing membrane 205.

Figure 3B:
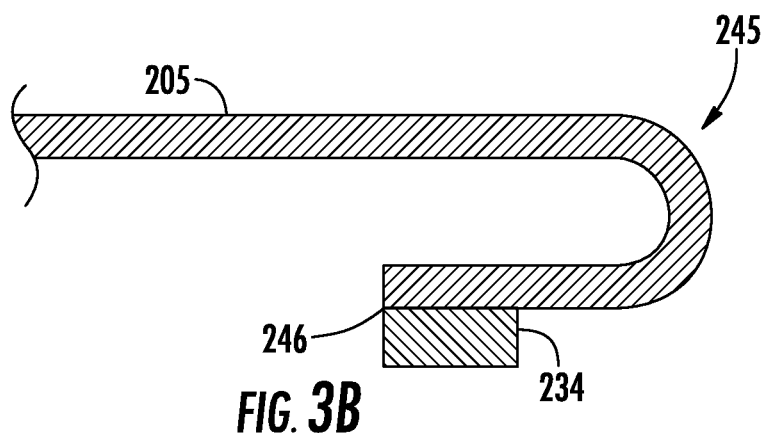
FIG. 3B is a cross-sectional end view of a portion of an example VCD according to one or more embodiments of the disclosure.

As is shown in FIG. 3B, the sealing membrane 205 is connected to the frame strut 234 of the support frame 210 at the connection point 246 using adhesive, welding, pins, staples, sutures, or any other coupling means. The sealing membrane 205 may be connected to the top side of the frame strut 234, as is shown. Alternatively, the sealing membrane 205 may be connected to the bottom side of the frame strut 234. The area of excess membrane 245 may be folded, including a single fold extending beyond the perimeter of the support frame 210 in the radial direction, as is shown. The fold may extend parallel to the surface defined by the sealing membrane 205.

Figure 3C:
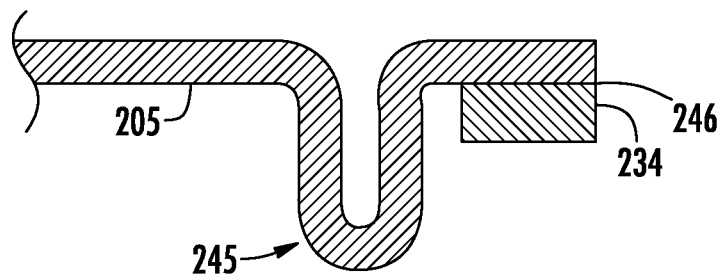
FIG. 3C is a cross-sectional end view of a portion of an example VCD according to one or more embodiments of the disclosure.

As is shown in FIG. 3C, the sealing membrane 205 is connected to the frame strut 234 of the support frame 210 at the connection point 246 using adhesive, welding, pins, staples, sutures, or any other coupling means. The sealing membrane 205 may be connected to the top side of the frame strut 234, as is shown. Alternatively, the sealing membrane 205 may be connected to the bottom side of the frame strut 234. The area of excess membrane 245 may be folded, including a single fold positioned within the perimeter of the support frame 210, as is shown. The fold may extend perpendicular to the surface defined by the sealing membrane 205. Further, the fold may be positioned below the surface defined by the sealing membrane 205, as is shown. Alternatively, the fold may be positioned above the surface defined by the sealing membrane 205.

Figure 3D:
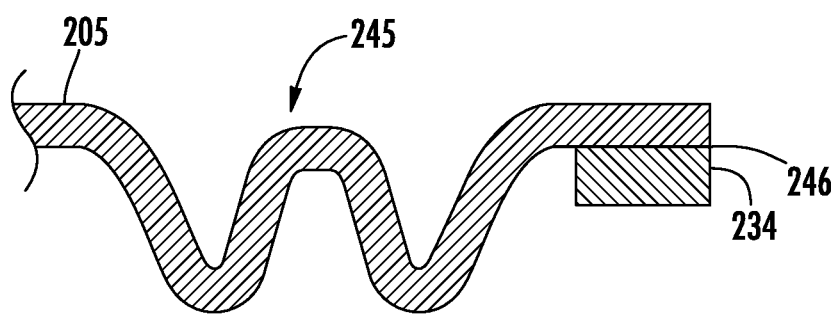
FIG. 3D is a cross-sectional end view of a portion of an example VCD according to one or more embodiments of the disclosure.

As is shown in FIG. 3D, the sealing membrane 205 is connected to the frame strut 234 of the support frame 210 at the connection point 246 using adhesive, welding, pins, staples, sutures, or any other coupling means. The sealing membrane 205 may be connected to the top side of the frame strut 234, as is shown. Alternatively, the sealing membrane 205 may be connected to the bottom side of the frame strut 234. The area of excess membrane 245 may be folded or wrinkled, including a plurality of folds or wrinkles positioned within the perimeter of the support frame 210, as is shown. The folds or wrinkles may extend perpendicular to the surface defined by the sealing membrane 205. Further, the folds or wrinkles may be positioned below the surface defined by the sealing membrane 205, as is shown. Alternatively, the folds or wrinkles may be positioned above the surface defined by the sealing membrane 205.

Figure 3E:
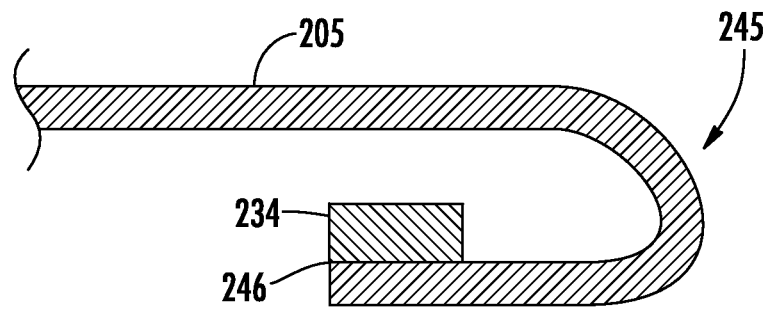
FIG. 3E is a cross-sectional end view of a portion of an example VCD according to one or more embodiments of the disclosure.

As is shown in FIG. 3E, the sealing membrane 205 is connected to the frame strut 234 of the support frame 210 at the connection point 246 using adhesive, welding, pins, staples, sutures, or any other coupling means. The sealing membrane 205 may be connected to the bottom side of the frame strut 234, as is shown. Alternatively, the sealing membrane 205 may be connected to the top side of the frame strut 234. The area of excess membrane 245 may be folded, including a single fold extending beyond the perimeter of the support frame 210 in the radial direction, as is shown. The fold may extend parallel to the surface defined by the sealing membrane 205.

Figure 3F:
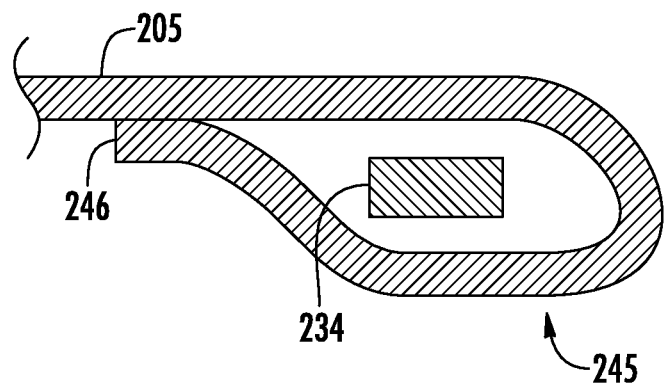
FIG. 3F is a cross-sectional end view of a portion of an example VCD according to one or more embodiments of the disclosure.

As is shown in FIG. 3F, the sealing membrane 205 is wrapped around the frame strut 234 of the support frame 210 and is coupled to itself at the connection point 246 using adhesive, solvent gluing, adhesive tape, pins, staples, sutures, or any other coupling means. The sealing membrane 205 may be coupled to itself on the bottom side of the sealing membrane 205, as is shown. Alternatively, the sealing membrane 205 may be coupled to itself on the top side of the sealing membrane 205. The area of excess membrane 245 may be formed as a loop extending beyond the perimeter of the support frame 210 in the radial direction. The loop may be substantially larger than the frame strut 234, as is shown. Because the loop is not rigidly coupled to the frame strut 234, the loop may be configured to slide or otherwise move with respect to the frame strut 234 as a result of tension generated in the sealing membrane 205.

Although the foregoing embodiments of the VCD 200 are primarily described as including the area of excess membrane 245 extending along the radial axis of the VCD 200, it will be understood that the area of excess membrane 245 alternatively may extend along the longitudinal axis of the VCD 200, or may extend along any other axis or area of the VCD 200. In some embodiments, the area of excess membrane 245 may extend over the full perimeter of the support frame 210. In some embodiments, the area of excess membrane 245 may vary over different regions along the perimeter of the support frame 210.

As discussed above, the sealing membrane 205 may be configured to deform and couple to the vessel wall of the vessel 10 upon expansion of the VCD 200 therein. The sealing membrane 205 may be substantially flexible and thus may be configured to adapt to the contour of the vessel wall due to force applied to the sealing membrane 205 by the blood pressure within the vessel 10. According to various embodiments, the sealing membrane 205 may be configured to elastically, visco-elastically, or plastically deform due to the force applied thereto by the blood pressure. As the sealing membrane 205 couples to the vessel wall, the vessel wall may limit deformation of the portions of the sealing membrane 205 positioned against the vessel wall. However, at the vessel puncture site 15, the vessel wall is injured and its ability to limit deformation of the portion of the sealing membrane 205 positioned over the vessel puncture site 15 may be substantially lower. It has now been discovered that in some cases where the sealing membrane 205 is substantially flexible, the portion of the sealing membrane 205 positioned over the vessel puncture site 15 may deform more than desired and may balloon through the vessel puncture site 15. Notably, the vessel wall generally includes radial muscles that induce radial reinforcement of the vessel 10. Upon insertion of a large bore sheath into the vessel 10, the main damage is along the radial axis of the vessel 10, with a more minor tear along the longitudinal axis of the vessel 10. Accordingly, the resulting vessel puncture site 15 generally has the form of a radially-extending slit or ellipse (not a true circle), with a length of the vessel puncture site 15 extending along the radial axis of the vessel 10. Moreover, the radial stress on the sealing membrane 205 (the stress generated along the radial axis thereof) is generally much higher than the longitudinal stress on the sealing membrane 205 (the stress generated along the longitudinal axis thereof). Accordingly, increasing resistance to deformation of the sealing membrane 205 along the radial axis thereof may be of particular importance.

Described herein are various embodiments of the VCD 200 that include means for limiting deformation of the sealing membrane 205 (i.e., increasing resistance to deformation of the sealing membrane 205), particularly along the portion of the sealing membrane 205 to be positioned over the vessel puncture site 15. In this manner, the sealing membrane 205 may withstand the pressure difference across the sealing membrane 205 without undesirable deformation. The various embodiments solve the above-described problem by including the cross-member support 215 extending across at least a portion of the sealing membrane 205 and configured to increase the sealing membrane's 205 resistance to deformation. The cross-member support 215 may be in the form of a flexible wire, such as a surgical suture material, as discussed above. In some embodiments of the VCD 200, the cross-member support 215 includes a plurality of wire segments extending between portions of the support frame 210 and configured to distribute forces applied to the sealing membrane 205.

FIGS. 4A-4D depict various embodiments of the VCD 200, showing top views thereof (the VCD 200 is shown in FIGS. 4A-4D in a flat, fully unrolled configuration for illustration purposes only). In these embodiments, the VCD 200 includes the cross-member support 215 extending across at least a portion of the sealing membrane 205 and configured to increase the sealing membrane's 205 resistance to deformation.

Figure 4A:
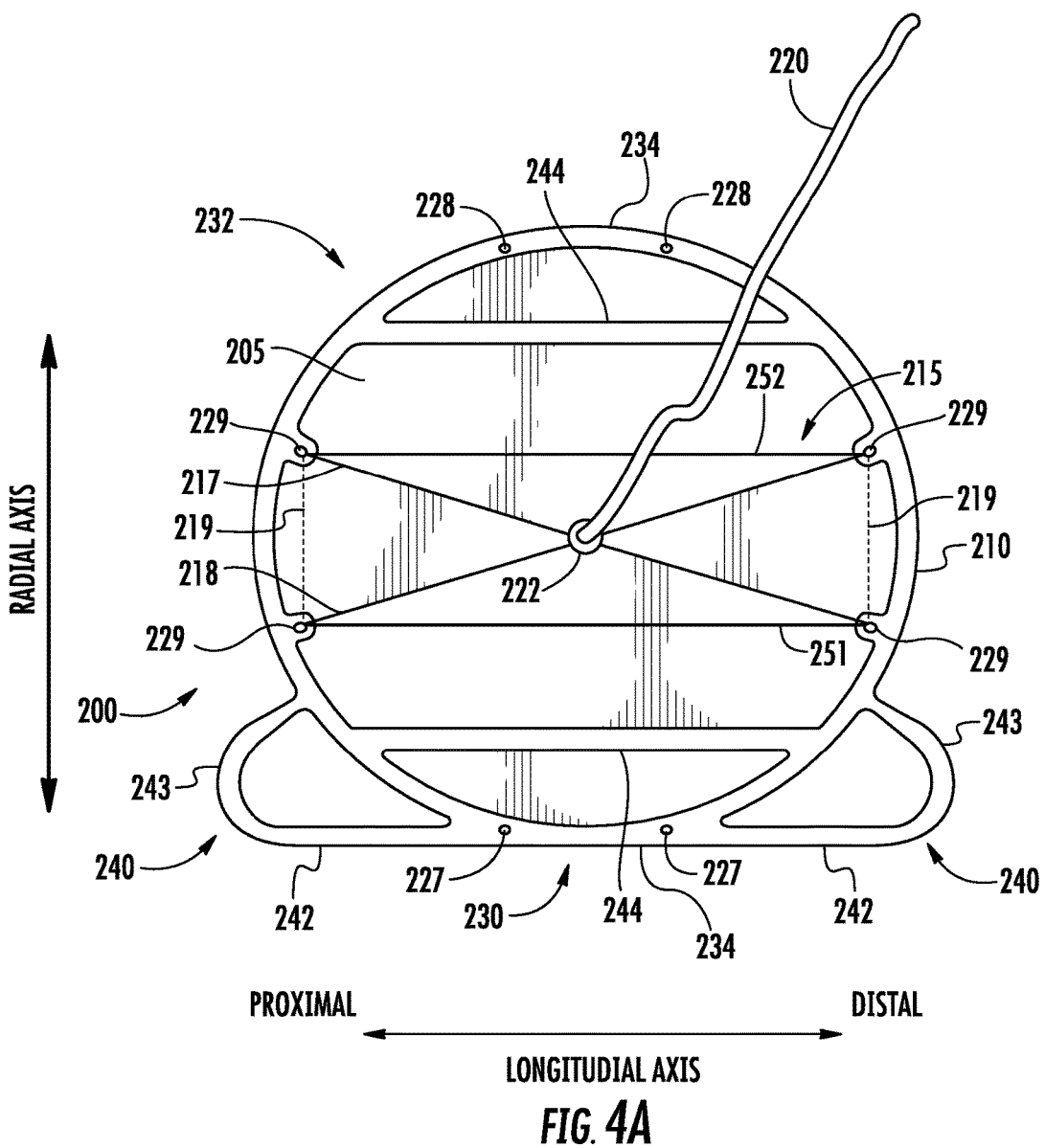
FIG. 4A is a top view of an example VCD according to one or more embodiments of the disclosure.

As is shown in FIG. 4A, the VCD 200 includes the cross-member support 215 configured in a manner similar to that described above with respect to FIG. 2B. In addition to the first and second wire segments 217, 218 extending between opposite sides of the support frame 210 and defining an X-shape, the cross-member support 215 also may include one or more longitudinal wire segments extending between opposite sides of the support frame 210 and along the longitudinal axis of the VCD 200. Specifically, as is shown, the cross-member support 215 includes a first longitudinal wire segment 251 and a second longitudinal wire segment 252 attached to the support frame 210 via the holes 229. In this manner, the first and second longitudinal wire segments 251, 252 may be configured to limit deformation of the sealing membrane 205, particularly along the longitudinal axis of the VCD 200. The first and second longitudinal wire segments 251, 252 may extend over the sealing membrane 205 and be configured to be positioned between the sealing membrane 205 and the vessel wall. Alternatively, the first and second longitudinal wire segments 251, 252 may extend beneath the sealing membrane 205 and be configured to be positioned between the sealing membrane 205 and the flow of blood through the vessel 10. In some embodiments, the first and second longitudinal wire segments 251, 252 are coupled to the sealing membrane 205 at one or more points by gluing, solvent bonding, or suturing. For example, the first and second longitudinal wire segments 251, 252 may be coupled to the sealing membrane 205 at the securing point 222 at about the center of the VCD 200 along the radial axis.

Figure 4B:
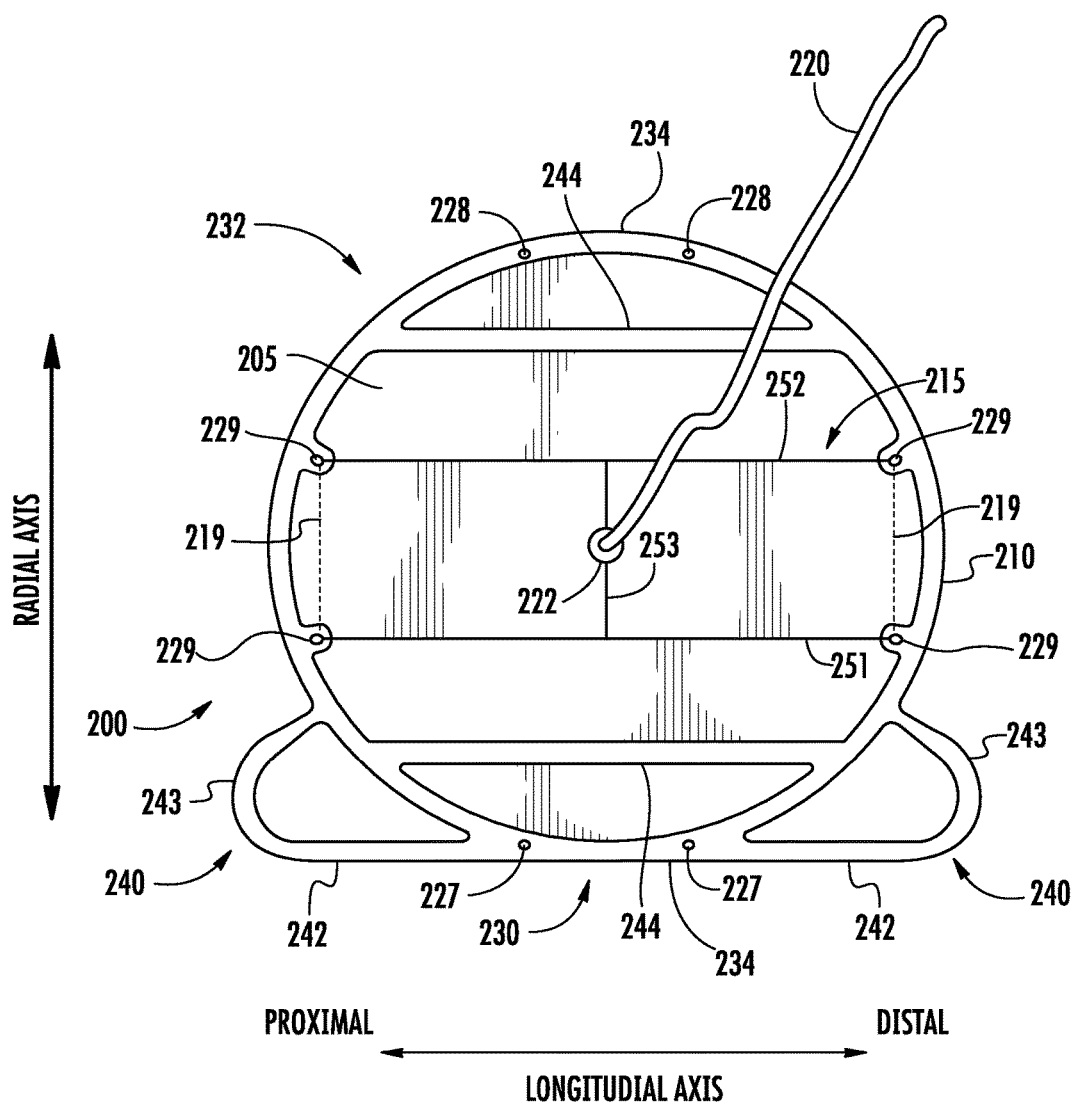
FIG. 4B is a top view of an example VCD according to one or more embodiments of the disclosure.

As is shown in FIG. 4B, the VCD 200 includes the cross-member support 215 including the first and second longitudinal wire segments 251, 252 configured in a manner similar to the embodiment of FIG. 4A. The cross-member support 215 also includes one or more radial wire segments extending between the first and second longitudinal wire segments 251, 252 and along the radial axis of the VCD 200. Specifically, the cross-member support 215 includes a radial wire segment 253 attached to the first and second longitudinal wire segments 251, 252, as is shown. In this manner, the radial wire segment 253 may be configured to limit deformation of the sealing membrane 205, particularly along the radial axis of the VCD 200. The radial wire segment 253 may extend over the sealing membrane 205 and be configured to be positioned between the sealing membrane 205 and the vessel wall. Alternatively, the radial wire segment 253 may extend beneath the sealing membrane 205 and be configured to be positioned between the sealing membrane 205 and the flow of blood through the vessel 10. In some embodiments, the radial wire segment 253 is coupled to the first and second longitudinal wire segments 251, 252 by wrapping, suturing, gluing, solvent bonding, thermal bonding, laser or ultrasonic welding, or another means of coupling. In some embodiments, the radial wire segment 253 is coupled to the sealing membrane 205 at one or more points by gluing, solvent bonding, or suturing. For example, the radial wire segment 253 may be coupled to the sealing membrane 205 at the securing point 222 at about the center of the VCD 200 along the radial axis.

Figure 4C:
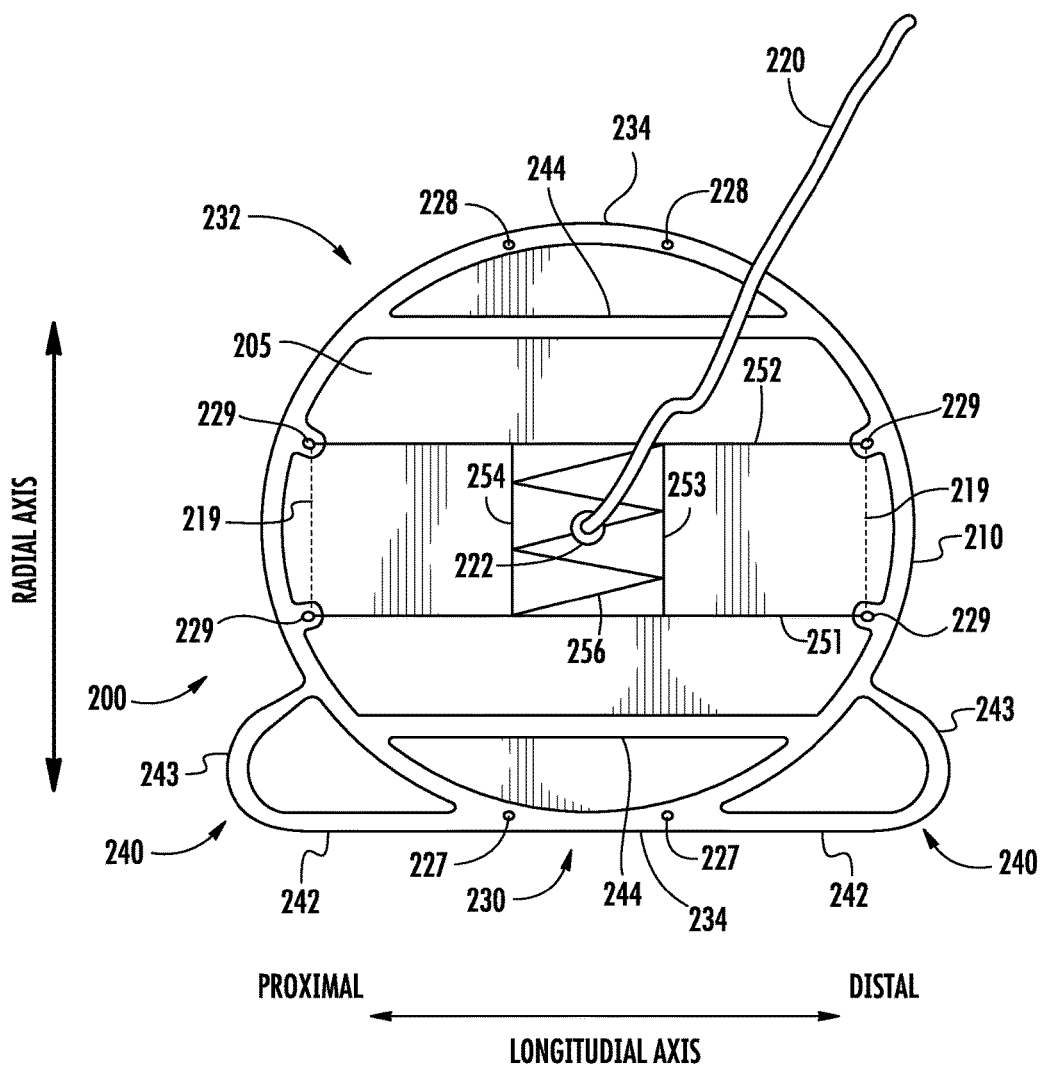
FIG. 4C is a top view of an example VCD according to one or more embodiments of the disclosure.

As is shown in FIG. 4C, the VCD 200 includes the cross-member support 215 including the first and second longitudinal wire segments 251, 252 configured in a manner similar to the embodiments of FIGS. 4A and 4B. The cross-member support 215 also includes a plurality of radial wire segments extending between the first and second longitudinal wire segments 251, 252 and along the radial axis of the VCD 200. Specifically, the cross-member support 215 includes a first radial wire segment 254 and a second radial wire segment 255 attached to the first and second longitudinal wire segments 251, 252, as is shown. The cross-member support 215 also includes one or more interconnecting wire segments 256 extending between the radial wire segments 254, 255. In this manner, the radial wire segments 254, 255 and the one or more interconnecting wire segments 256 may be configured to limit deformation of the sealing membrane 205, particularly along the radial axis of the VCD 200. The one or more interconnecting wire segments 256 may define a zig-zag shape, as is shown. The one or more interconnecting wire segments 256 may extend over the sealing membrane 205 and be configured to be positioned between the sealing membrane 205 and the vessel wall. Alternatively, the one or more interconnecting wire segments 256 may extend beneath the sealing membrane 205 and be configured to be positioned between the sealing membrane 205 and the flow of blood through the vessel 10. In some embodiments, the one or more interconnecting wire segments 256 are coupled to the radial wire segments 254, 255 by wrapping, suturing, gluing, solvent bonding, thermal bonding, laser or ultrasonic welding, or another means of coupling. The one or more interconnecting wire segments 256 may be formed of a single wire extending back and forth between the radial wire segments 254, 255. Alternatively, the one or more interconnecting wire segments 256 may be formed of multiple wires each extending between the radial wire segments 254, 255. In some embodiments, the one or more interconnecting wire segments 256 are coupled to the sealing membrane 205 at one or more points by gluing, solvent bonding, or suturing. For example, the one or more interconnecting wire segments 256 may be coupled to the sealing membrane 205 at the securing point 222 at about the center of the VCD 200 along the radial axis.

Figure 4D:
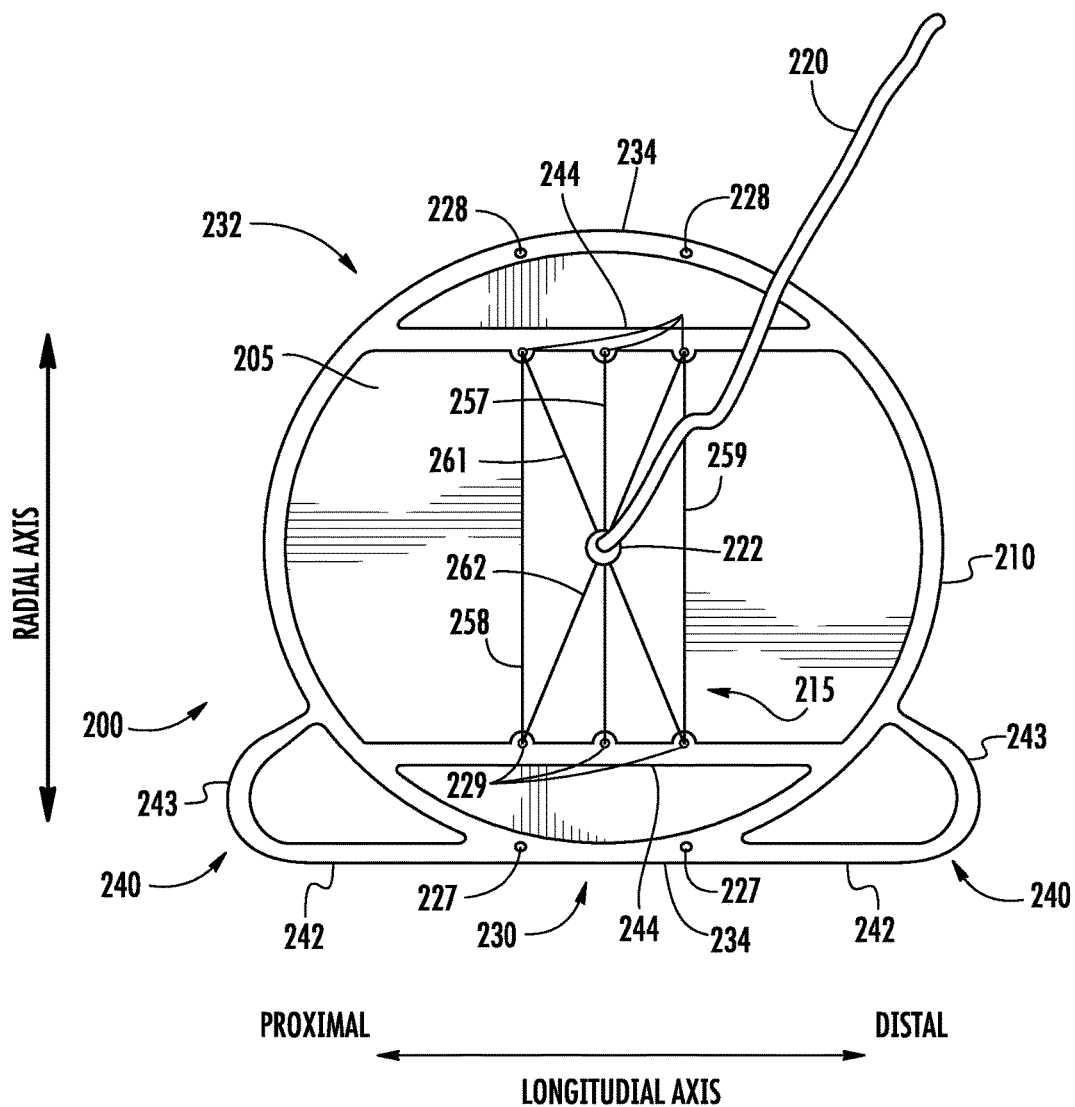
FIG. 4D is a top view of an example VCD according to one or more embodiments of the disclosure.

As is shown in FIG. 4D, the VCD 200 includes the cross-member support 215 including a plurality of radial wire segments extending between the longitudinal supports 244 and along the radial axis of the VCD 200. Specifically, the cross-member support 215 includes a first radial wire segment 257, a second radial wire segment 258, and a third radial wire segment 259 attached to and extending perpendicular to the longitudinal supports 244, as is shown. The cross-member support 215 also includes one or more diagonal wire segments extending diagonally between the longitudinal supports 244. Specifically, the cross-member support 215 includes a first diagonal wire segment 261 and a second diagonal wire segment 262 attached to and extending diagonally between the longitudinal supports 244. In this manner, the radial wire segments 257, 258, 259 and the diagonal wire segments 261, 262 may be configured to limit deformation of the sealing membrane 205, particularly along the radial axis of the VCD 200. The diagonal wire segments 261, 262 may define an X-shape, as is shown. The radial wire segments 257, 258, 259 and the diagonal wire segments 261, 262 may extend over the sealing membrane 205 and be configured to be positioned between the sealing membrane 205 and the vessel wall. Alternatively, the radial wire segments 257, 258, 259 and the diagonal wire segments 261, 262 may extend beneath the sealing membrane 205 and be configured to be positioned between the sealing membrane 205 and the flow of blood through the vessel 10. In some embodiments, the radial wire segments 257, 258, 259 and the diagonal wire segments 261, 262 are coupled to the longitudinal supports 244 via holes 229 defined in the longitudinal supports 244. In some embodiments, one or more of the radial wire segments 257, 258, 259 and the diagonal wire segments 261, 262 are coupled to the sealing membrane 205 at one or more points by gluing, solvent bonding, or suturing. For example, the first radial wire segment 257 and the diagonal wire segments 261, 262 may be coupled to the sealing membrane 205 at the securing point 222 at about the center of the VCD 200 along the radial axis. Although the cross-member support 215 of the VCD 200 shown in FIG. 4D includes the three radial wire segments 257, 258, 259 and the two diagonal wire segments 261, 262, other embodiments may omit one or more of these wire segments. For example, in some embodiments, the cross-member support 215 includes only the first radial wire segment 257 and the diagonal wire segments 261, 262. In other embodiments, the cross-member support 215 includes only the second and third radial wire segments 258, 259 and the diagonal wire segments 261, 262. In still other embodiments, the cross-member support 215 includes only the second and third radial wire segments 258, 259.

As discussed above, the sealing membrane 205 may be configured to deform and couple to the vessel wall of the vessel 10 upon expansion of the VCD 200 therein. The sealing membrane 205 may be substantially flexible and thus may be configured to adapt to the contour of the vessel wall due to force applied to the sealing membrane 205 by the blood pressure within the vessel 10. In some embodiments, a highly flexible sealing membrane 205 is desirable, allowing the sealing membrane 205 to couple to the vessel wall due to the force applied by the blood pressure, even for challenging vessel contours. As the sealing membrane 205 couples to the vessel wall, the vessel wall may limit deformation of the portions of the sealing membrane 205 positioned against the vessel wall. However, at the vessel puncture site 15, the vessel wall is injured and its ability to limit deformation of the portion of the sealing membrane 205 positioned over the vessel puncture site 15 may be substantially lower. It has now been discovered that in some cases where the sealing membrane 205 is highly flexible, the portion of the sealing membrane 205 positioned over the vessel puncture site 15 may be too weak to withstand the pressure difference across the sealing membrane 205. Accordingly, increasing the strength of the portion of the sealing membrane 205 to be positioned over the vessel puncture site 15 may be of particular importance.

Described herein are various embodiments of the VCD 200 that include means for increasing the strength and the pressure resistance of the portion of the sealing membrane 205 to be positioned over the vessel puncture site 15. In this manner, the sealing membrane 205 may withstand the pressure difference across the sealing membrane 205 without undesirable deformation, weakening, or failure thereof. The various embodiments solve the above-described problem by including a patch extending along a portion of the sealing membrane 205 and configured to increase the strength and the pressure resistance of the portion of the sealing membrane 205 to be positioned over the vessel puncture site 15.

FIGS. 5A-5D depict various embodiments of the VCD 200, showing top views thereof (the VCD 200 is shown in FIGS. 5A-5D in a flat, fully unrolled configuration for illustration purposes only). FIG. 5E depicts the VCD 200 according to one or more embodiments of the disclosure (the VCD 200 is shown in FIG. 5E in a curved, partially unrolled configuration). In these embodiments, the VCD 200 includes a support patch 270 extending along a portion of the sealing membrane 205 and configured to increase the strength and the pressure resistance of the portion of the sealing membrane 205 to be positioned over the vessel puncture site 15.

Figure 5A:
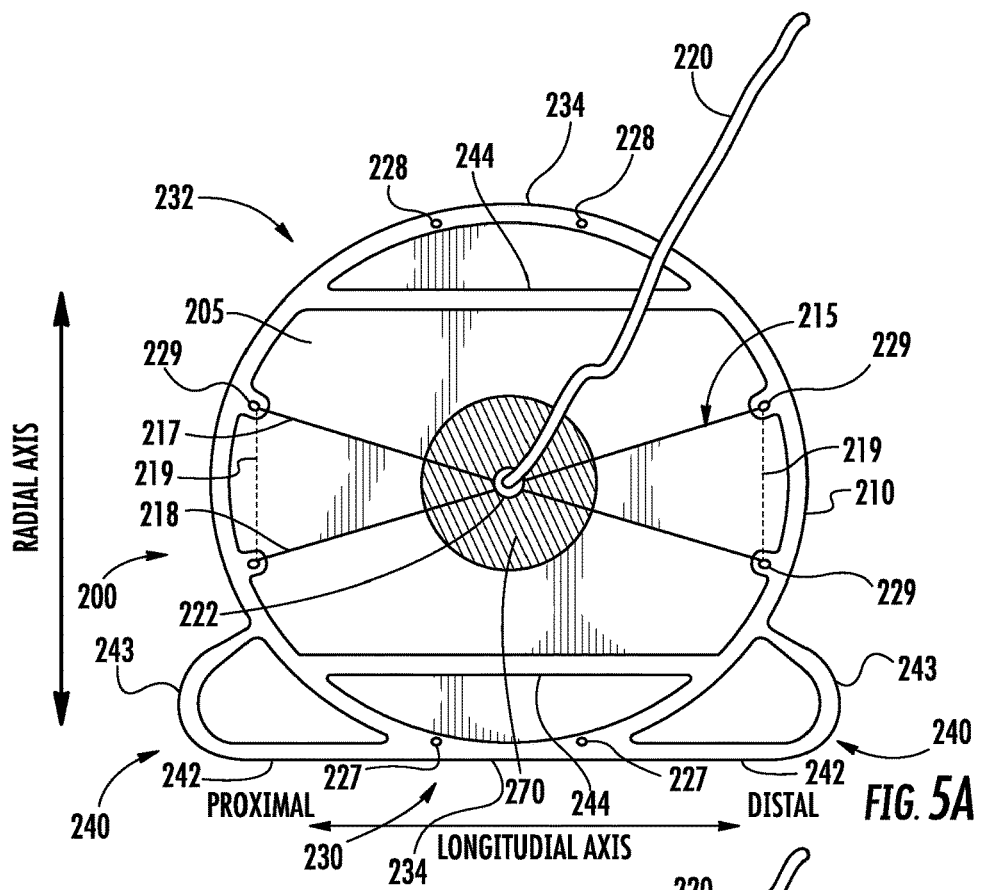
FIG. 5A is a top view of an example VCD according to one or more embodiments of the disclosure.
Figure 5B:
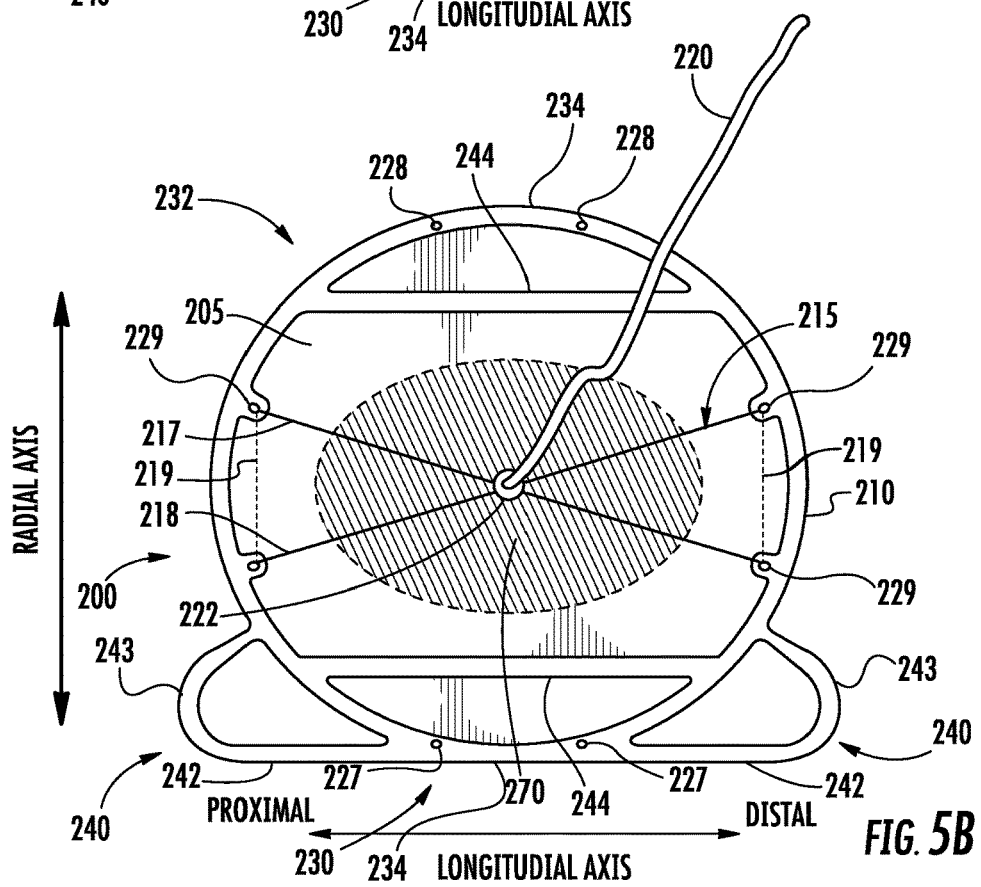
FIG. 5B is a top view of an example VCD according to one or more embodiments of the disclosure.
Figure 5C:
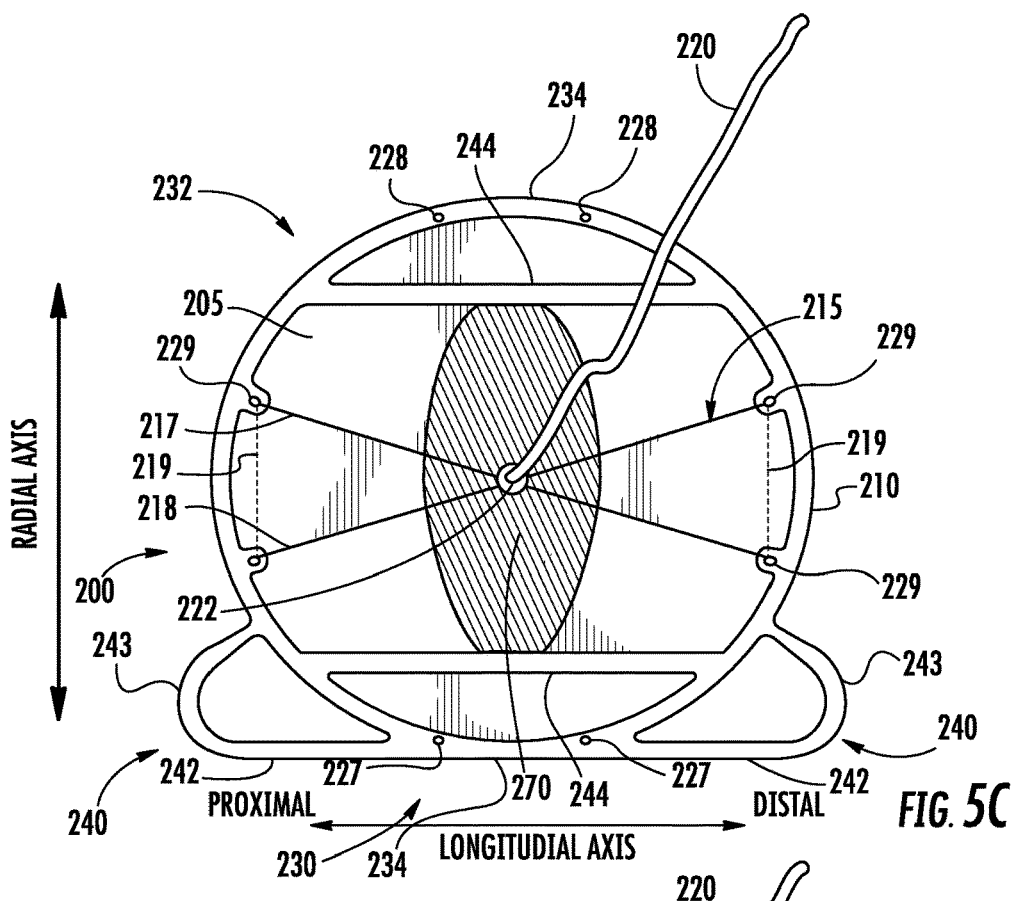
FIG. 5C is a top view of an example VCD according to one or more embodiments of the disclosure.
Figure 5D:
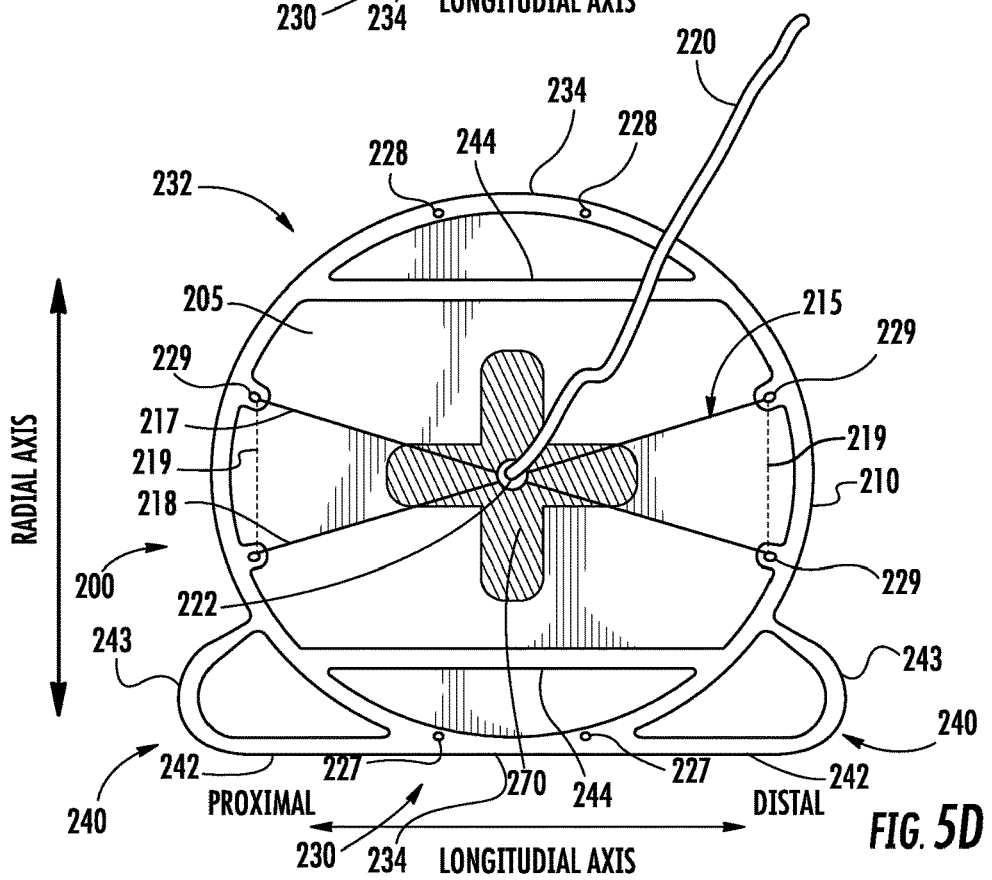
FIG. 5D is a top view of an example VCD according to one or more embodiments of the disclosure.
Figure 5E:
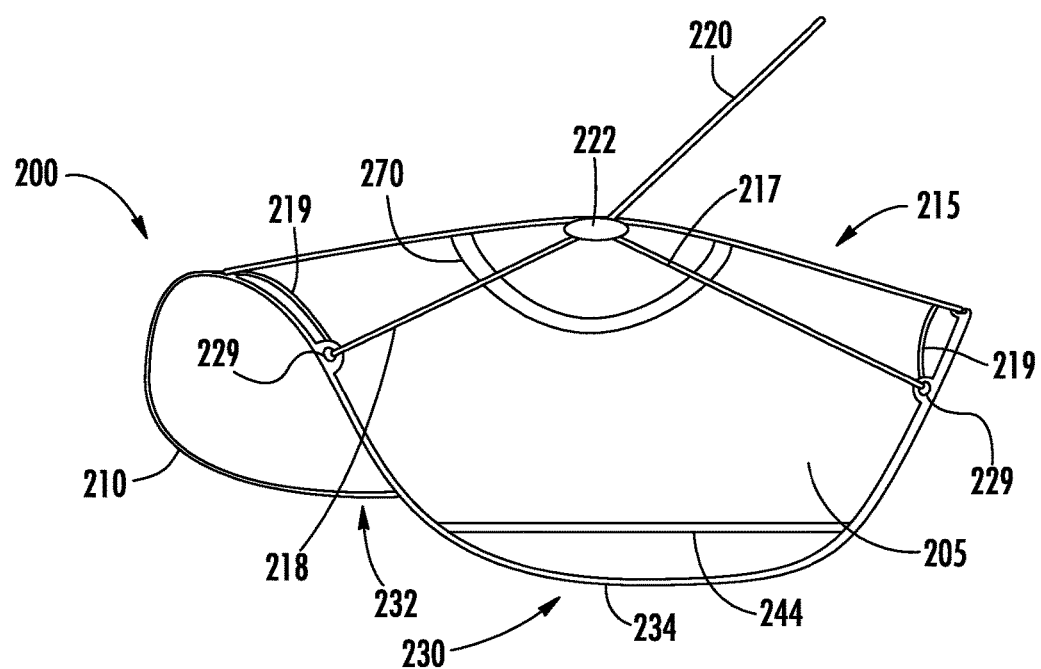
FIG. 5E is a perspective view of an example VCD according to one or more embodiments of the disclosure.

As is shown in FIGS. 5A-5E, the VCD 200 includes the patch 270 positioned about the center of the sealing membrane 205, and thus a center of the VCD 200, such that the patch 270 substantially covers the portion of the sealing membrane 205 to be positioned over the vessel puncture site 15 during use of the VCD 200. The patch 270 may have a circular shape, as is shown in FIGS. 5A and 5E, an elliptical shape, as is shown in FIGS. 5B and 5C, or a plus-shape (+), as is shown in FIG. 5D. In various other embodiments, the patch 270 may have other shapes, such as a square shape, a rectangular shape, an oval shape, an X-shape, or any variation or combination of such shapes. As discussed above, the vessel wall generally includes radial muscles that induce radial reinforcement of the vessel 10, and upon insertion of a large bore sheath into the vessel 10 and dilation of the resulting vessel puncture site 15, the main damage is along the radial axis of the vessel 10, with a more minor tear along the longitudinal axis of the vessel 10. Accordingly, the vessel puncture site 15 generally has the form of a radially-extending slit or ellipse (not a true circle), with a length of the vessel puncture site 15 extending along the radial axis of the vessel 10. Moreover, the radial stress on the sealing membrane 205 (the stress generated along the radial axis thereof) is generally much higher than the longitudinal stress on the sealing membrane 205 (the stress generated along the longitudinal axis thereof). Accordingly, the elliptical shaped patch 270 shown in FIG. 5C may be particularly advantageous, as the major axis of the elliptical shape extends along the radial axis of the VCD 200 and thus increases the strength of the sealing membrane 205 thereabout against the higher radial forces.

In some embodiments, the patch 270 is coupled to the sealing membrane 205, as is shown in FIGS. 5A-5D. The patch 270 may be coupled to the sealing membrane 205 by any suitable means including, but not limited to, mechanical coupling, glue, adhesive, solvent adhesive, welding (e.g., by heat or laser), or suturing. In some embodiments, the patch 270 is at least partially coupled to the longitudinal supports 244, as is shown in FIG. 5C. The patch 270 may be at least partially coupled to the longitudinal supports 244 in addition to or instead of being coupled to or connected to the sealing membrane 205. The patch 270 may extend over the sealing membrane 205 and be configured to be positioned between the sealing membrane 205 and the puncture site 15 of the vessel wall. Alternatively, the patch 270 may extend beneath the sealing membrane 205 and be configured to be positioned between the sealing membrane 205 and the flow of blood through the vessel 10. In some embodiments, the VCD 200 includes a plurality of patches 270 extending along a portion, or a plurality of portions, of the sealing membrane 205. For example, the VCD 200 may include two patches 270 in a "sandwich" configuration about the sealing membrane 205, with a first patch 270 extending over the sealing membrane 205 and configured to be positioned between the sealing membrane 205 and the puncture site 15 of the vessel wall, and a second patch 270 extending beneath the sealing membrane 205 and configured to be positioned between the sealing membrane 205 and the flow of blood through the vessel 10. The two patches 270 may have the same shape and may extend along the same portion of the sealing membrane 205, or the two patches 270 may have different shapes and may extend along different portions of the sealing membrane 205.

In some embodiments, the patch 270 is coupled to the cross-member support 215 instead of the sealing membrane 205, as is shown in FIG. 5E. The patch 270 may be coupled to the cross-member support 215 by any suitable means including, but not limited to, mechanical coupling, glue, adhesive, solvent adhesive, welding (e.g., by heat or laser), or suturing. The patch 270 may be coupled to the cross-member support 215 at any point along the cross-member support 215. In some embodiments, the patch 270 is coupled to the cross-member support 215 at the securing point 222. In other embodiments, the patch 270 is coupled to the cross-member support 215 along adjacent portions of the first wire segment 217 and the second wire segment 218. During use of the VCD 200 shown in FIG. 5E, as the blood pressure within the vessel 10 pushes on and stretches the sealing membrane 205, the portion of the sealing membrane 205 extending over the puncture site 15 stretches outwardly until it comes into contact with the patch 270. Because the patch 270 is securely coupled to the cross-member support 215 at about the center of the puncture site 15, the patch 270 advantageously supports the portion of the sealing membrane 205 extending over the puncture site 15 and thereby prevents any additional significant expansion, weakening, or possible failure of sealing membrane 205.

The patch 270 may be formed of the same material as sealing membrane 205, with similar or different properties (e.g., thickness, flexibility, strength, etc.). Alternatively, the patch 270 may be formed of a different material than the sealing membrane 205, with similar or different properties. In some embodiments, the patch 270 is formed of a biocompatible material. Examples of suitable biocompatible materials of construction of the patch 270 include, but are not limited to, expanded polytetrafluoroethylene (ePTFE), polyethylene, polypropylene, polyester, polyurethane, silicone, Dacron, urethane, polyaryletheretherketone (PEEK), stainless steel, titanium, nickel-titanium, cobalt, nickel-chromium, gold, platinum, and/or any composite, alloy, as well as any composite or combination of the foregoing materials or other suitable materials. In some embodiments, the patch 270 is partially or completely formed of a biodegradable material. Examples of suitable biodegradable materials of construction of the patch 270 include, but are not limited to, modified cellulose, collagen, fibrin, fibrinogen, elastin, or other connective proteins or natural materials; polymers or copolymers (such as, but not limited to, polylactide (e.g., poly-L-lactide (PLLA), poly-D-lactide (PDLA)), polyglycolide, polydioxanone, polycaprolactone, polygluconate, polylactic acid (PLA), polylactic acid-polyethylene oxide copolymers, poly(hydroxybutyrate), polyanhydride, polyphosphoester, poly(amino acids), poly(alpha-hydroxy acid), or any other similar copolymers); magnesium or magnesium alloys; or aluminum or aluminum alloys; as well as any composite or combination of the foregoing materials or other biodegradable materials, which, after a period of time resorb into the body of the patient. The patch 270 may have a thickness similar to or different from that of the sealing membrane 205. In various embodiments, the patch 270 has a thickness from about 5 µm to about 500 µm, from about 25 µm to about 250 µm, or from about 50 µm to about 150 µm.

Although the foregoing embodiments of the VCD 200 are described as including the patch 270 formed separately from and coupled to or positioned about the sealing membrane 205, the patch 270 may be formed as a part of the sealing membrane 205 according to other embodiments. In some embodiments, the patch 270 is a part of the sealing membrane 205 that has been treated chemically to locally increase its strength (relative to an untreated part of the sealing membrane 205). For example, a local reaction with an oxidizer, such as oxygen, water, alcohols, hydrogen peroxide, ethylene oxide may cause some biodegradable materials (e.g., PLA, PGA, PCL) to become stiffer, thereby increasing their ability to withstand fluid pressure. The local reaction may be performed by either protecting/shielding the remainder of the sealing membrane 205 during a treatment process (e.g., coating the surface area to be protected with an inert protecting material) or depositing the reactant material only on a preselected or target location of the sealing membrane 205 to form the patch 270 at that location. In some other embodiments, the patch 270 is a part of the sealing membrane 205 that has been heated or exposed to radiation (e.g., laser irradiation) to locally increase its strength (relative to an untreated part of the sealing membrane 205). In still other embodiments, the patch 270 is a part of the sealing membrane 205 over which the thickness of the sealing membrane 205 has been increased to locally increase its strength (relative to a remainder of the sealing membrane 205). According to these embodiments, the patch 270 may function in a manner similar to that described above to increase the strength and the pressure resistance of the portion of the sealing membrane 205 to be positioned over the vessel puncture site 15.

Figure 6A:
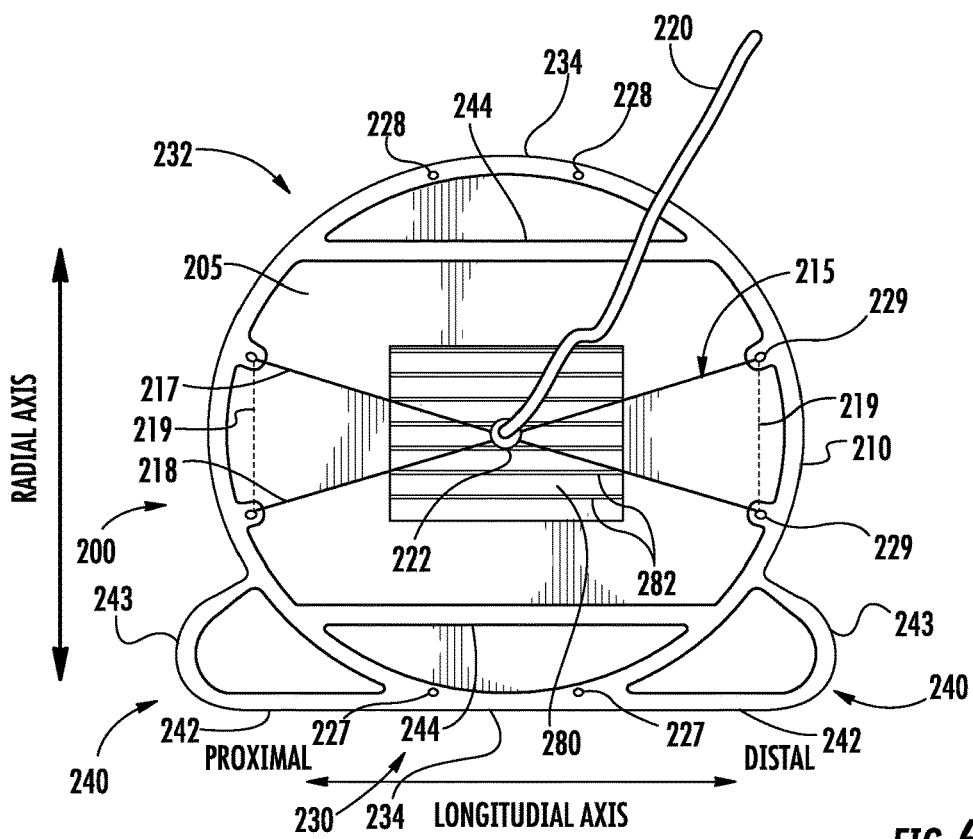
FIG. 6A is a top view of an example VCD according to one or more embodiments of the disclosure.
Figure 6B:
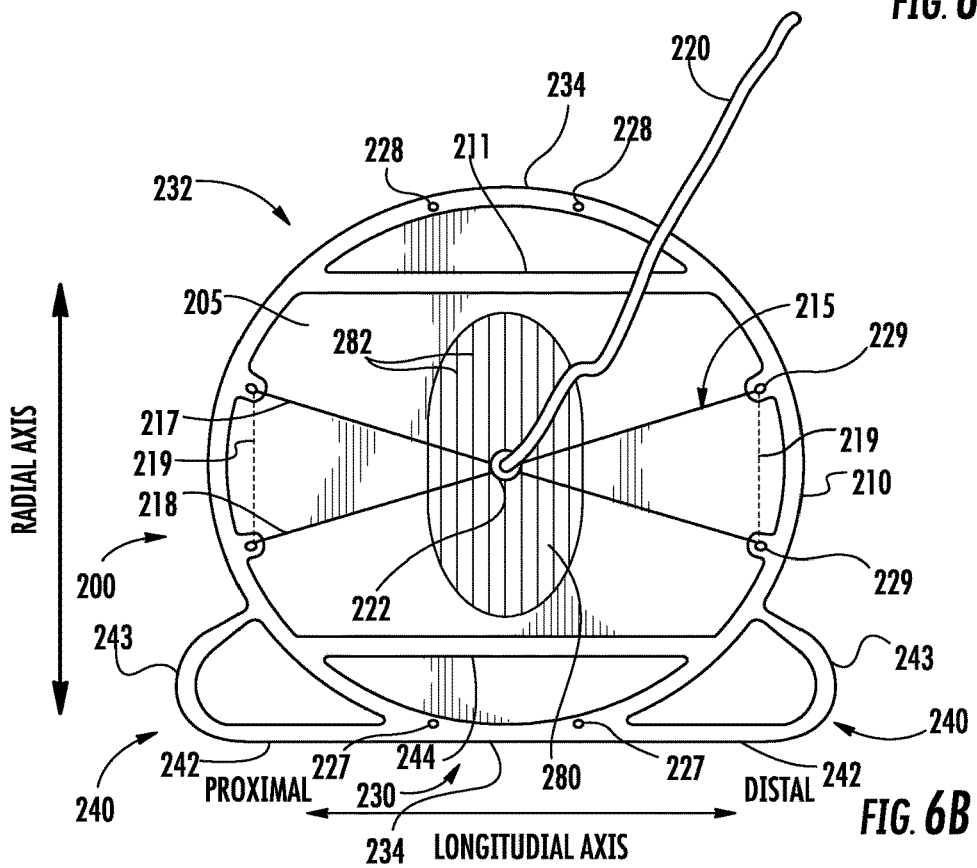
FIG. 6B is a top view of an example VCD according to one or more embodiments of the disclosure.
Figure 6C:
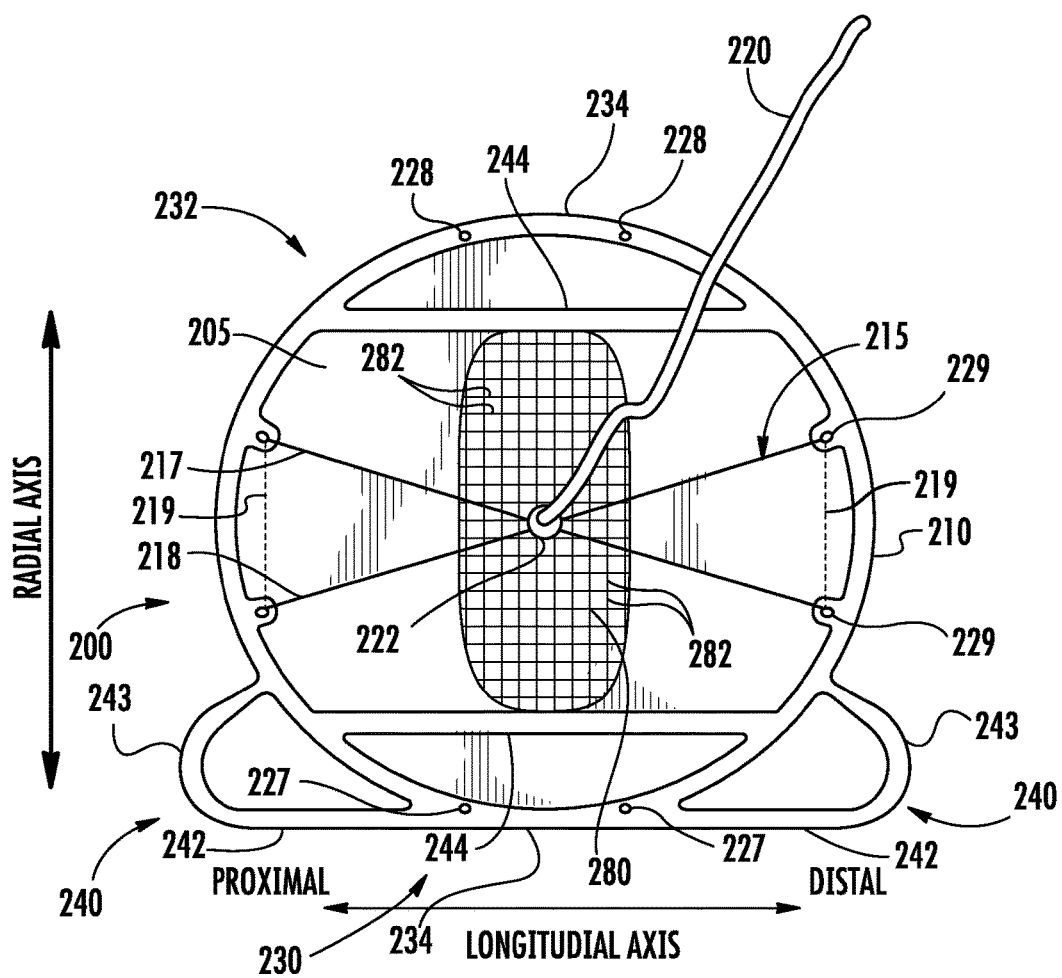
FIG. 6C is a top view of an example VCD according to one or more embodiments of the disclosure.

FIGS. 6A-6C depict various embodiments of the VCD 200, showing top views thereof (the VCD 200 is shown in FIGS. 6A-6C in a flat, fully unrolled configuration for illustration purposes only). In these embodiments, the VCD 200 includes a support patch 280 extending along a portion of the sealing membrane 205 and configured to increase the strength and the pressure resistance of the portion of the sealing membrane 205 to be positioned over the vessel puncture site 15.

As is shown in FIGS. 6A-6C, the VCD 200 includes the patch 280 positioned about the center of the sealing membrane 205, and thus a center of the VCD 200, such that the patch 280 substantially covers the portion of the sealing membrane 205 to be positioned over the vessel puncture site 15 during use of the VCD 200. The patch 280 includes an array of wires, ribbons, or strands 282 extending about the sealing membrane 205, as is shown. In some embodiments, and is shown in FIG. 6A, the wires, ribbons, or strands 282 extend parallel to the longitudinal axis of the VCD 200 and thus parallel to longitudinal axis of the vessel 10 and the flow of blood therethrough when the VCD 200 is deployed within the vessel 10. In some other embodiments, as is shown in FIGS. 6B and 6C, the wires, ribbons, or strands 282 extend perpendicular to the longitudinal axis of the VCD 200 (i.e., parallel to the radial axis of the VCD 200) and thus perpendicular to longitudinal axis of the vessel 10 and the flow of blood therethrough when the VCD 200 is deployed within the vessel 10. In still other embodiments, the wires, ribbons, or strands 282 extend at an angle of about 30°, about 45°, or about 60° to the longitudinal axis of the VCD 200 and thus at an angle of about 30°, about 45°, or about 60° to longitudinal axis of the vessel 10 and the flow of blood therethrough when the VCD 200 is deployed within the vessel 10.

In some embodiments, the array of wires, ribbons, or strands 282 of the patch 280 are arranged as a mesh or a web, as is shown in FIG. 6C. In this manner, a first group of the wires, ribbons, or strands 282 extend in a first direction, while a second group of the wires, ribbons, or strands 282 extending in a second direction, which may be perpendicular to the first direction. In some embodiments, the wires, ribbons, or strands 282 of one of the groups extend parallel to the longitudinal axis of the VCD 200 and thus parallel to longitudinal axis of the vessel 10 and the flow of blood therethrough when the VCD 200 is deployed within the vessel 10. In some other embodiments, the wires, ribbons, or strands 282 of one of the groups extend perpendicular to the longitudinal axis of the VCD 200 (i.e., parallel to the radial axis of the VCD 200) and thus perpendicular to longitudinal axis of the vessel 10 and the flow of blood therethrough when the VCD 200 is deployed within the vessel 10. In still other embodiments, the wires, ribbons, or strands 282 of one of the groups extend at an angle of about 30°, about 45°, or about 60° to the longitudinal axis of the VCD 200 and thus at an angle of about 30°, about 45°, or about 60° to longitudinal axis of the vessel 10 and the flow of blood therethrough when the VCD 200 is deployed within the vessel 10.

The patch 280 may have a rectangular shape, as is shown in FIG. 6A, or an elliptical shape, as is shown in FIGS. 6B and 6C. In various other embodiments, the patch 280 may have other shapes, such as a circular shape, an oval shape, a square shape, a plus-shape (+), an X-shape, or any variation or combination of such shapes. As discussed above, the vessel wall generally includes radial muscles that induce radial reinforcement of the vessel 10, and upon insertion of a large bore sheath into the vessel 10 and dilation of the resulting vessel puncture site 15, the main damage is along the radial axis of the vessel 10, with a more minor tear along the longitudinal axis of the vessel 10. Accordingly, the vessel puncture site 15 generally has the form of a radially-extending slit or ellipse (not a true circle), with a length of the vessel puncture site 15 extending along the radial axis of the vessel 10. Moreover, the radial stress on the sealing membrane 205 (the stress generated along the radial axis thereof) is generally much higher than the longitudinal stress on the sealing membrane 205 (the stress generated along the longitudinal axis thereof). Accordingly, the elliptical shaped patch 280 shown in FIGS. 6B and 6C may be particularly advantageous, as the major axis of the elliptical shape extends along the radial axis of the VCD 200 and thus increases the strength of the sealing membrane 205 thereabout against the higher radial forces.

In some embodiments, the patch 280 is coupled to the sealing membrane 205, as is shown in FIGS. 6A-6C. The patch 280 may be coupled to the sealing membrane 205 by any suitable means including, but not limited to, mechanical coupling, glue, adhesive, solvent adhesive, welding (e.g., by heat or laser), or suturing. In some embodiments, the patch 280 is at least partially coupled to the longitudinal supports 244, as is shown in FIG. 6C. The patch 280 may be at least partially coupled to the longitudinal supports 244 in addition to or instead of being coupled to or connected to the sealing membrane 205. The patch 280 may extend over the sealing membrane 205 and be configured to be positioned between the sealing membrane 205 and the puncture site 15 of the vessel wall. Alternatively, the patch 280 may extend beneath the sealing membrane 205 and be configured to be positioned between the sealing membrane 205 and the flow of blood through the vessel 10. In some embodiments, the VCD 200 includes a plurality of patches 280 extending along a portion, or a plurality of portions, of the sealing membrane 205. For example, the VCD 200 may include two patches 280 in a "sandwich" configuration about the sealing membrane 205, with a first patch 280 extending over the sealing membrane 205 and configured to be positioned between the sealing membrane 205 and the puncture site 15 of the vessel wall, and a second patch 280 extending beneath the sealing membrane 205 and configured to be positioned between the sealing membrane 205 and the flow of blood through the vessel 10. The two patches 280 may have the same shape and may extend along the same portion of the sealing membrane 205, or the two patches 280 may have different shapes and may extend along different portions of the sealing membrane 205.

In some embodiments, the wires, ribbons, or strands 282 are formed of a biocompatible material. Examples of suitable biocompatible materials of construction of the wires, ribbons, or strands 282 include, but are not limited to, expanded polytetrafluoroethylene (ePTFE), polyethylene, polypropylene, polyester, polyurethane, silicone, Dacron, urethane, polyaryletheretherketone (PEEK), stainless steel, titanium, nickel-titanium, cobalt, nickel-chromium, gold, platinum, and/or any composite, alloy, as well as any composite or combination of the foregoing materials or other suitable materials. In some embodiments, the wires, ribbons, or strands 282 are partially or completely formed of a biodegradable material. Examples of suitable biodegradable materials of construction of the wires, ribbons, or strands 282 include, but are not limited to, modified cellulose, collagen, fibrin, fibrinogen, elastin, or other connective proteins or natural materials; polymers or copolymers (such as, but not limited to, polylactide (e.g., poly-L-lactide (PLLA), poly-D-lactide (PDLA)), polyglycolide, polydioxanone, polycaprolactone, polygluconate, polylactic acid (PLA), polylactic acid-polyethylene oxide copolymers, poly(hydroxybutyrate), polyanhydride, polyphosphoester, poly(amino acids), poly(alpha-hydroxy acid), or any other similar copolymers); magnesium or magnesium alloys; or aluminum or aluminum alloys; as well as any composite or combination of the foregoing materials or other biodegradable materials, which, after a period of time resorb into the body of the patient. In some embodiments, the patch 280 includes a polymer substrate, with the array of the wires, ribbons, or strands 282 embedded within the polymer substrate. In this manner, the polymer substrate may reinforce the array of the wires, ribbons, or strands 282 embedded therein. The wires, ribbons, or strands 282 may have a round, square, or rectangular cross-section. In some embodiments, the cross-section of the wires, ribbons, or strands 282 has a thickness dimension from about 1 µm to about 500 µm, from about 5 µm to about 100 µm, or from about 10 µm to about 50 µm.

Although the foregoing embodiments of the VCD 200 are described as including the patch 280 formed separately from and coupled to or positioned about the sealing membrane 205, the patch 280 may formed as a part of the sealing membrane 205 according to other embodiments. In some embodiments, the sealing membrane 205 may be formed with the wires, ribbons, or strands 282 embedded within the sealing membrane 205. For example, the wires, ribbons, or strands 282 may be positioned within a mold, and the sealing membrane 205 may be cast with the wires, ribbons, or strands 282 embedded therein. According to these embodiments, the patch 280 may function in a manner similar to that described above to increase the strength and the pressure resistance of the portion of the sealing membrane 205 to be positioned over the vessel puncture site 15.

Delivery Systems and Methods of Delivering a Vasculature Closure Device

During delivery of the various embodiments of the VCD 200 into the vessel 10, bleeding may occur due to a decrease of the profile of a delivery system passing through the vessel puncture 15. For example, bleeding may occur during removal of an introducer sheath of the delivery system. Alternatively, bleeding may occur due to a failed closure of the vessel puncture 15. Because the vessel puncture 15 may be a relatively large arterial puncture, substantial blood loss may be life threatening and thus an ability to control bleeding from the vessel puncture 15 may be crucial. According to a previously-disclosed delivery system and method for delivering a VCD, a balloon may be placed within the vessel 10 proximal to the vessel puncture site 15 and inflated before or during delivery of the VCD. The balloon may be delivered via the contralateral limb or some other arterial access approach, such as a radial or carotid access approach. In this manner, the previously-disclosed delivery method requires an additional arterial access point as well as complex navigation and manipulation for positioning the balloon at the ipsilateral limb artery.

Described herein are an example delivery system and method for delivering the VCD 200, which control bleeding from the vessel puncture 15 while eliminating the need for an additional arterial access point. In this manner, the delivery system and method simplify the procedure of closing the vessel puncture 15 with the VCD 200. FIGS. 7A-7D depict a delivery system 300 and different stages of delivering and securing the VCD 200 within a vessel 10 according to various embodiments.

FIG. 7A shows the vessel 10 following a therapeutic procedure carried out through an introducer sheath 330 positioned through the vessel puncture 15. After removal of the instruments used to carry out the procedure, the delivery system 300 is used to deliver the VCD 200. The delivery system 300 includes a balloon catheter 302 that is introduced through the introducer sheath 330 and into the vessel 10, as is shown. The balloon catheter 302 may include a shaft 304 and an expandable balloon 306 positioned about a distal end of the shaft 304. The balloon catheter 302 also may include a luer lock adapter 308 or other connection means positioned about a proximal end of the shaft 304. The shaft 304 may include a first lumen extending therethrough from the luer lock adapter 308 to the balloon 306 and configured for inflating the balloon 306. The shaft 304 also may include a second lumen extending therethrough and configured for passing a guide wire (not shown) through the balloon catheter 302. The balloon 306 may be configured to have a low profile when deflated for delivery into and removal from the vessel 10, and a high profile when inflated for controlling blood flow within the vessel 10. When the balloon 306 is inflated, its diameter may be configured to control blood flow within the vessel 10. In some embodiments, the inflated diameter of the balloon 306 is configured to substantially occlude blood flow through the vessel 10.

According to various embodiments, the balloon 306 may be a compliant balloon, a semi-compliant balloon, or a fully compliant balloon. A "compliant" balloon is a balloon that changes in diameter according to a pressure within the balloon. A "non-compliant" balloon is a balloon that maintains a substantially fixed diameter following initial inflation (i.e., the diameter of the balloon is substantially independent of further increases in pressure within the balloon). The balloon 306 may be an embolectomy balloon indicated for vessel occlusion. For example, the balloon 306 may be a commercially-available embolectomy balloon manufactured by LeMaitre Vascular, Inc. or Arrow International, Inc. The balloon 306 may have a deflated profile of between about 3 Fr and about 5 Fr and may be configured for occluding the vessel 10 having a diameter of about 6 mm to about 10 mm.

FIG. 7B shows the delivery system 300 following introduction and positioning of the balloon 306 as well as introduction of the VCD 200 into the vessel 10. The balloon 306 is inflated using a syringe 310 or other inflation means attached to the luer lock adapter 308. Inflation of the balloon 306 may be carried out using a liquid (such as saline, a medical-imaging contrast medium, or a mixture of saline and a medical-imaging contrast medium) or a gas (such as helium or carbon dioxide). Depending on the desired result, the balloon 306 is inflated to a diameter sufficiently large enough to control or to occlude blood flow within the vessel 10 during implantation of the VCD 200. FIG. 7C shows the delivery system 300 following removal of the introducer sheath 330 and deployment of the VCD 200 (i.e., allowing the VCD 200 to unroll into an expanded state, as is shown). After deployment of the VCD 200, the balloon 306 is deflated and removed from the vessel 10. During removal of the balloon 306, tension may be maintained on the tether 220 to prevent movement of the VCD 200 within the vessel 10. During this stage of the closure procedure, some bleeding may occur as the shaft 304 and the balloon 306 pass between the VCD 200 and the vessel wall. FIG. 7D shows the final result after the balloon catheter 302 is removed and the VCD 200 is deployed in the vessel 10 and positioned to cover the vessel puncture site 15. Ultimately, the delivery system 300 and method for delivering the VCD 200 may simplify the procedure of closing the vessel puncture by allowing the balloon 306 to be delivered through the same access site (the vessel puncture site 15) as the VCD 200.

Although the foregoing embodiments of the method for delivering the VCD 200 are described as including introduction of the balloon 306 through the vessel puncture site 15 to reach the target location, alternative embodiments may include introduction of the balloon 306 through another access site into the same groin (i.e., ipsilateral access). According to various embodiments, the other access site may be more proximal to the vessel puncture site 15 or more distal to the vessel puncture site 15. The other access site may include a relatively small puncture, such as about 6 Fr, as would be sufficient for introducing the balloon 306.

It is appreciated that many modifications and variations of the devices, systems, and methods described herein, such as dimensional, size, and/or shape variations, will be apparent to those skilled in the art from the foregoing detailed description. Such modifications and variations are intended to come within the scope of the appended claims.

We claim:

1. A vasculature closure device, comprising:
an expandable support frame deployable within a vessel and configured to expand from a collapsed configuration into an expanded configuration; and
a sealing membrane at least partially supported by the support frame;
wherein the support frame is configured to intraluminally move the sealing membrane against a puncture site existing in a wall of the vessel when the support frame is in the expanded configuration across the puncture site within the vessel;
wherein the device has a longitudinal axis configured to align with a length of the vessel and a radial axis perpendicular to the longitudinal axis; and
wherein the sealing membrane comprises an area of excess membrane comprising one or more folds or one or more wrinkles defined by overlapping regions of the sealing membrane when the support frame is in the expanded configuration and configured to allow extension of the area of excess membrane relative to the support frame along the radial axis of the device when the support frame is in the expanded configuration to facilitate coupling of the sealing membrane to the wall of the vessel.

2. The vasculature closure device of claim 1, wherein the area of excess membrane is positioned along a perimeter of the sealing membrane.

3. The vasculature closure device of claim 1, wherein the support frame extends along the perimeter of the sealing membrane.

4. The vasculature closure device of claim 1, wherein the area of excess membrane comprises one or more folds configured to allow extension of the area of excess membrane along the radial axis of the device.

5. The vasculature closure device of claim 4, wherein the one or more folds comprise a first fold and a second fold positioned adjacent to one another and forming an S-shape.

6. The vasculature closure device of claim 4, wherein the one or more folds are positioned within a perimeter of the support frame.

7. The vasculature closure device of claim 4, wherein the one or more folds extend beyond a perimeter of the support frame.

8. The vasculature closure device of claim 4, wherein the one or more folds at least partially overlap the support frame.

9. The vasculature closure device of claim 4, wherein the one or more folds are connected to the support frame.

10. The vasculature closure device of claim 1, wherein the area of excess membrane comprises a plurality of wrinkles configured to allow extension of the area of excess membrane along the radial axis of the device.

11. The vasculature closure device of claim 10, wherein the plurality of wrinkles are positioned adjacent to the support frame.

12. The vasculature closure device of claim 10, wherein the plurality of wrinkles are positioned within a perimeter of the support frame.

13. The vasculature closure device of claim 1, wherein the area of excess membrane is positioned along a perimeter of the sealing membrane, and wherein the support frame extends along the perimeter of the sealing membrane.

14. The vasculature closure device of claim 1, wherein the area of excess membrane is positioned about a center of the sealing membrane along the radial axis of the device.

15. The vasculature closure device of claim 1, wherein the area of excess membrane is positioned about a radial end of the sealing membrane along the radial axis of the device.

16. The vasculature closure device of claim 1, wherein the area of excess membrane is spaced apart from the support frame.

17. The vasculature closure device of claim 1, wherein the sealing membrane comprises a first area of excess membrane and a second area of excess membrane spaced apart from one another along the radial axis of the device.

18. The vasculature closure device of claim 1, wherein the sealing membrane comprises a first area of excess membrane positioned about a first radial end of the sealing membrane along the radial axis of the device, and a second area of excess membrane positioned about a second radial end of the sealing membrane along the radial axis of the device.

19. The vasculature closure device of claim 1, wherein the area of excess membrane is formed by the sealing membrane being larger than the support frame by about 0.1 millimeters to about 10 millimeters along the radial axis of the device.

20. The vasculature closure device of claim 1, wherein the area of excess membrane is formed by the sealing membrane being larger than the support frame by about 1 millimeter to about 10 millimeters along the radial axis of the device.

21. The vasculature closure device of claim 1, wherein the area of excess membrane is formed by the sealing membrane being larger than the support frame by about 2 millimeters to about 4 millimeters along the radial axis of the device.

22. A method for sealing a puncture site in a vessel wall of a patient, the method comprising:
deploying a balloon catheter through the puncture site and into the vessel;
deploying the vasculature closure device of claim 1 through the puncture site and into the vessel; and
securing at least a portion of the vasculature closure device against the puncture site for sealing thereabout.

23. The method of claim 22, further comprising, prior to deploying the vasculature closure device through the puncture, inflating a balloon of the balloon catheter to control blood flow within the vessel.

24. The vasculature closure device of claim 1, further comprising a cross-member support extending across at least a portion of the sealing membrane, wherein the cross-member support comprises a pair of wire segments extending between opposite sides of the support frame.

25. The vasculature closure device of claim 1, further comprising a cross-member support extending across at least a portion of the sealing membrane, wherein the cross-member support comprises a pair of longitudinal wire segments extending between opposite sides of the support frame and parallel to one another along the longitudinal axis of the device.

26. The vasculature closure device of claim 1, further comprising a cross-member support extending across at least a portion of the sealing membrane, wherein the support frame comprises a pair of longitudinal supports extending across at least a portion of the sealing membrane and parallel to one another along the longitudinal axis of the device, and wherein the cross-member support comprises a pair of radial wire segments extending between the pair of longitudinal supports and parallel to one another along the radial axis of the device.

27. The vasculature closure device of claim 1, further comprising a patch extending along a portion of the sealing membrane and having a perimeter that is smaller than a perimeter of the sealing membrane.

28. The vasculature closure device of claim 1, further comprising a cross-member support extending across at least a portion of the sealing membrane, wherein the cross-member support comprises a rigid member extending between opposite sides of the support frame along the longitudinal axis of the device.

29. A vasculature closure device, comprising:
an expandable support frame deployable within a vessel;
a sealing membrane at least partially supported by the support frame; and
a cross-member support extending across at least a portion of the sealing membrane;
wherein the device is configured to intraluminally position the sealing membrane against a puncture site existing in a wall of the vessel when the support frame is in an expanded configuration across the puncture site within the vessel;
wherein the device has a longitudinal axis configured to align with a length of the vessel; and
wherein the cross-member support comprises a pair of longitudinal wire segments extending between opposite sides of the support frame and parallel to one another along the longitudinal axis of the device.

30. A vasculature closure device, comprising:
an expandable support frame deployable within a vessel;
a sealing membrane at least partially supported by the support frame; and
a cross-member support extending across at least a portion of the sealing membrane;
wherein the device is configured to intraluminally position the sealing membrane against a puncture site existing in a wall of the vessel when the support frame is in an expanded configuration across the puncture site within the vessel;
wherein the device has a longitudinal axis configured to align with a length of the vessel and a radial axis perpendicular to the longitudinal axis;
wherein the support frame comprises a pair of longitudinal supports extending across at least a portion of the sealing membrane and parallel to one another along the longitudinal axis of the device; and wherein the cross-member support comprises a pair of radial wire segments extending between the pair of longitudinal supports and parallel to one another along the radial axis of the device.

* * * * *